(12) United States Patent
Voth

(10) Patent No.: US 8,364,253 B2
(45) Date of Patent: *Jan. 29, 2013

(54) SYSTEM AND METHOD FOR MAPPING ELECTROPHYSIOLOGY INFORMATION ONTO COMPLEX GEOMETRY

(75) Inventor: Eric Jon Voth, Maplewood, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 247 days.

This patent is subject to a terminal disclaimer.

(21) Appl. No.: 12/822,474

(22) Filed: Jun. 24, 2010

(65) Prior Publication Data

US 2010/0274123 A1    Oct. 28, 2010

Related U.S. Application Data

(63) Continuation of application No. 11/647,276, filed on Dec. 29, 2006, now Pat. No. 7,774,051.

(60) Provisional application No. 60/800,848, filed on May 17, 2006.

(51) Int. Cl.
*A61B 5/04* (2006.01)

(52) U.S. Cl. ........................................................ 600/523

(58) Field of Classification Search ................... 600/523
See application file for complete search history.

(56) References Cited

U.S. PATENT DOCUMENTS

| | | |
|---|---|---|
| 5,228,442 A | 7/1993 | Imran |
| 5,231,995 A | 8/1993 | Desai |
| 5,239,999 A | 8/1993 | Imran |
| 5,279,299 A | 1/1994 | Imran |
| 5,297,549 A | 3/1994 | Beatty et al. |
| 5,385,148 A | 1/1995 | Lesh et al. |
| 5,391,199 A | 2/1995 | Ben-Haim |
| 5,403,311 A | 4/1995 | Abele et al. |
| 5,406,946 A | 4/1995 | Imran |
| 5,411,025 A | 5/1995 | Webster, Jr. |
| 5,445,148 A | 8/1995 | Jaraczewski et al. |
| 5,480,422 A | 1/1996 | Ben-Haim |
| 5,487,757 A | 1/1996 | Truckai et al. |
| 5,545,200 A | 8/1996 | West et al. |
| 5,546,951 A | 8/1996 | Ben-Haim |
| 5,562,619 A | 10/1996 | Mirarchi et al. |
| 5,568,809 A | 10/1996 | Ben-Haim |
| 5,571,088 A | 11/1996 | Lennox et al. |
| 5,575,766 A | 11/1996 | Swartz et al. |
| 5,575,772 A | 11/1996 | Lennox |
| 5,584,872 A | 12/1996 | LaFontaine et al. |
| 5,607,462 A | 3/1997 | Imran |
| 5,611,777 A | 3/1997 | Bowden et al. |
| 5,626,136 A | 5/1997 | Webster, Jr. |
| 5,628,313 A | 5/1997 | Webster, Jr. |
| 5,656,028 A | 8/1997 | Swartz et al. |
| 5,662,108 A | 9/1997 | Budd et al. |

(Continued)

OTHER PUBLICATIONS

Kuklik, P et al., "The reconstruction from a set of points, and analysis of the interior surface of the heart chamber", *Physiological Measuremen, Institute of Physics Publishing*, Bristol GB vol. 3 Jun. 25, 2004, 617-627.

(Continued)

*Primary Examiner* — George Manuel
(74) *Attorney, Agent, or Firm* — Wiley Rein LLP

(57) ABSTRACT

The instant invention relates to an electrophysiology apparatus and method used to measure electrical activity occurring in a portion of tissue of a patient and to visualize the electrical activity and/or information related to the electrical activity. In particular, the instant invention relates to three-dimensional mapping of the electrical activity and/or the information related to the electrical activity.

13 Claims, 15 Drawing Sheets

U.S. PATENT DOCUMENTS

| | | | |
|---|---|---|---|
| 5,687,737 A | 11/1997 | Branham et al. |
| 5,690,611 A | 11/1997 | Swartz et al. |
| 5,694,945 A | 12/1997 | Ben-Haim |
| 5,697,377 A | 12/1997 | Wittkampf |
| 5,718,241 A | 2/1998 | Ben-Haim et al. |
| 5,722,401 A | 3/1998 | Pietroski et al. |
| 5,738,096 A | 4/1998 | Ben-Haim |
| 5,772,590 A | 6/1998 | Webster, Jr. |
| 5,782,239 A | 7/1998 | Webster, Jr. |
| 5,782,828 A | 7/1998 | Chen et al. |
| 5,782,900 A | 7/1998 | de la Rama et al. |
| 5,800,413 A | 9/1998 | Swartz et al. |
| 5,807,249 A | 9/1998 | Qin et al. |
| 5,814,028 A | 9/1998 | Swartz et al. |
| 5,820,568 A | 10/1998 | Willis |
| 5,826,576 A | 10/1998 | West |
| 5,827,272 A | 10/1998 | Breining et al. |
| 5,836,875 A | 11/1998 | Webster, Jr. |
| 5,840,025 A | 11/1998 | Ben-Haim |
| 5,849,028 A | 12/1998 | Chen |
| 5,860,974 A | 1/1999 | Abele |
| 5,865,800 A | 2/1999 | Mirarchi et al. |
| 5,868,741 A | 2/1999 | Chia et al. |
| 5,891,027 A | 4/1999 | Tu et al. |
| 5,891,137 A | 4/1999 | Chia et al. |
| 5,897,529 A | 4/1999 | Ponzi |
| 5,902,289 A | 5/1999 | Swartz et al. |
| 5,908,446 A | 6/1999 | Imran |
| 5,916,158 A | 6/1999 | Webster, Jr. |
| 5,916,213 A | 6/1999 | Haissaguerre et al. |
| 5,935,063 A | 8/1999 | Nguyen |
| 5,935,102 A | 8/1999 | Bowden et al. |
| 5,938,694 A | 8/1999 | Jaraczewski et al. |
| 5,947,938 A | 9/1999 | Swartz et al. |
| 5,954,665 A | 9/1999 | Ben-Haim |
| 5,964,796 A | 10/1999 | Imran |
| 5,983,126 A | 11/1999 | Wittkampf |
| 5,987,344 A | 11/1999 | West |
| 6,001,095 A | 12/1999 | de la Rama et al. |
| 6,002,955 A | 12/1999 | Willems et al. |
| 6,004,269 A | 12/1999 | Crowley et al. |
| 6,023,638 A | 2/2000 | Swanson |
| 6,027,473 A | 2/2000 | Ponzi |
| 6,029,091 A | 2/2000 | de la Rama et al. |
| 6,059,739 A | 5/2000 | Baumann |
| 6,063,022 A | 5/2000 | Ben-Haim |
| 6,066,094 A | 5/2000 | Ben-Haim |
| 6,066,126 A | 5/2000 | Li et al. |
| 6,068,629 A | 5/2000 | Haissaguerre et al. |
| 6,068,653 A | 5/2000 | LaFontaine |
| 6,090,084 A | 7/2000 | Hassett et al. |
| 6,090,104 A | 7/2000 | Webster, Jr. |
| 6,115,626 A | 9/2000 | Whayne et al. |
| 6,169,916 B1 | 1/2001 | West |
| 6,171,275 B1 | 1/2001 | Webster, Jr. |
| 6,187,032 B1 | 2/2001 | Ohyu et al. |
| 6,210,362 B1 | 4/2001 | Ponzi |
| 6,212,426 B1 | 4/2001 | Swanson |
| 6,221,070 B1 | 4/2001 | Tu et al. |
| 6,226,542 B1 * | 5/2001 | Reisfeld ........................ 600/407 |
| 6,233,477 B1 | 5/2001 | Chia et al. |
| 6,235,021 B1 | 5/2001 | Sieben |
| 6,235,044 B1 | 5/2001 | Root et al. |
| 6,241,722 B1 | 6/2001 | Dobak et al. |
| 6,241,726 B1 | 6/2001 | Chia et al. |
| 6,277,077 B1 | 8/2001 | Brisken et al. |
| 6,301,496 B1 | 10/2001 | Reisfeld |
| 6,314,962 B1 | 11/2001 | Vaska et al. |
| 6,314,963 B1 | 11/2001 | Vaska et al. |
| 6,443,894 B1 | 9/2002 | Sumanaweera et al. |
| 6,456,867 B2 | 9/2002 | Reisfeld |
| 6,640,119 B1 | 10/2003 | Budd et al. |
| 6,672,312 B2 | 1/2004 | Acker |
| 6,685,732 B2 | 2/2004 | Kramer |
| 6,689,128 B2 | 2/2004 | Sliwa, Jr. et al. |
| 6,701,931 B2 | 3/2004 | Sliwa, Jr. et al. |
| 6,728,562 B1 | 4/2004 | Budd et al. |
| 6,743,227 B2 | 6/2004 | Seraj et al. |
| 6,837,886 B2 | 1/2005 | Collins et al. |
| 6,858,026 B2 | 2/2005 | Sliwa, Jr. et al. |
| 6,939,309 B1 | 9/2005 | Beatty et al. |
| 6,947,785 B1 | 9/2005 | Beatty et al. |
| 6,974,373 B2 | 12/2005 | Kriesel |
| 6,978,168 B2 | 12/2005 | Beatty et al. |
| 6,990,370 B1 | 1/2006 | Beatty et al. |
| 7,214,128 B2 | 5/2007 | Kriesel |
| 7,231,075 B2 | 6/2007 | Raghavan et al. |
| 7,774,051 B2 | 8/2010 | Voth |
| 2001/0009974 A1 | 7/2001 | Reisfeld |
| 2003/0028090 A1 | 2/2003 | Raghavan et al. |
| 2004/0254437 A1 | 12/2004 | Hauck et al. |
| 2005/0140680 A1 | 6/2005 | Boyd et al. |
| 2006/0015096 A1 | 1/2006 | Hauck et al. |
| 2006/0050987 A1 | 3/2006 | Shimada et al. |
| 2006/0095022 A1 | 5/2006 | Moll et al. |
| 2006/0100610 A1 | 5/2006 | Wallace et al. |
| 2006/0290695 A1 | 12/2006 | Salomie |
| 2007/0060833 A1 | 3/2007 | Hauck |
| 2007/0073179 A1 | 3/2007 | Afonso et al. |
| 2007/0197929 A1 * | 8/2007 | Porath et al. .................. 600/523 |

OTHER PUBLICATIONS

Souag, N , "Three dimensional reconstruction of the left ventricle based on the Delaunay Triangulation", *Signal Processing and Information Technology, 2004* Proceedings of the Fourth IEEE International Symposium, Rome, Italy Dec. 18-21, 2004, Piscataway, NH Dec. 12-18, 2004, 539-542.

Surazhsky, Vitaly et al., "Fast Exact and Approximate Geodesics on Meshes", *Conference SIGGRAPH 2005*.

Barber, C.B., et al., "The Quickhull Algorithm for Convex Hulls", pp. 1-15, (reprint of same titled article as published in ACM Transactions on Mathematical Software), vol. 22, No. 4, pp. 469-483, Dec. 1996.

Nademanee, Koonlawee, M.D., FACC, et al., "A New Approach for Catheter Ablation of Atrial Fibrillation: Mapping of the Electrophysiological Substrate", Journal of the American College of Cardiology, vol. 43, No. 11, pp. 2044-2053, 2004. (downloaded from content. onlinejacc.org on Jun. 6, 2007).

Pachon, Jose, et al., "A new treatment for atrial fibrillation based on spectral analysis to guide the catheter RF-ablation", Europace, vol. 6, pp. 590-601, 2004.

International Search Report issued in PCT/US07/68980, dated Jan. 11, 2008.

* cited by examiner

SYSTEM AND METHOD FOR MAPPING ELECTROPHYSIOLOGY INFORMATION ONTO COMPLEX GEOMETRY

CROSS-REFERENCE TO RELATED APPLICATIONS

This application is a continuation of U.S application Ser. No. 11/647,276, filed 29 Dec. 2006, now U.S. Pat. No. 7,774,051, issued 10 Aug. 2010, which claims the benefit of U.S. provisional patent application No. 60/800,848, filed 17 May 2006. Each of the foregoing is incorporated by reference as though fully set forth herein.

The following applications are also incorporated by reference as though fully set forth herein: U.S. application Ser. Nos. 11/227,006, filed 15 Sep. 2005, now U.S. Pat. No. 8,038,625, issued 18 Oct. 2011; 10/819,027, filed 6 Apr. 2004, now U.S. Pat. No. 7,263,397, issued 28 Aug. 2007; Ser. No. 11/647,275, filed 29 Dec. 2006, now U.S. Pat. No. 7,988,634, issued 2 Aug. 2011, which claims the benefit of U.S. provisional application No. 60/800,858, filed 17 May 2006; and 11/647,298, filed 29 Dec. 2006, which claims the benefit of U.S. provisional application No. 60/851,042, filed 12 Oct. 2006, and which is a continuation-in-part of U.S. application Ser. No. 11/139,908, filed 27 May 2005, now U.S. Pat. No. 7,632,265, issued 15 Dec. 2009, which claims the benefit of U.S. provisional application No. 60/575,411, filed 28 May 2004.

BACKGROUND OF THE INVENTION

1. Field of the Invention

The instant invention relates to an electrophysiology apparatus and method used to measure electrical activity occurring in a portion of tissue of a patient and to visualize the electrical activity and/or information related to the electrical activity. In particular, the instant invention relates to three-dimensional mapping of the electrical activity and/or the information related to the electrical activity.

2. Background Art

The present invention relates to the creation of electrophysiological maps of the human anatomy, including for example, an electrophysiology map of the human heart.

Conventional modeling systems exist for generating a three-dimensional model of the heart utilizing technology such as CT scan, MRI, radar imaging, x-ray imaging, and fluoroscopic imaging. Such data is often processed using a three-dimensional modeling technique. Such imaging technology is often useful in preparing a patient for treatment and/or surgery, and typically, the imaging process is performed hours and in some cases days in advance of the treatment and/or surgery.

During the treatment and/or surgery, conventional systems are available that can generate an electrophysiology map for the patient. An electrophysiology map is especially useful in connection with the diagnosis and treatment of atrial fibrillation of a patient's heart. The points at which the electrophysiology data is measured, however, rarely correspond to the data points that define the three-dimensional model prepared in advance of the treatment.

Accordingly, a need exists for an improvement that can relate electrophysiology data to a three-dimensional surface model of a patient's anatomy.

BRIEF SUMMARY OF THE INVENTION

The present invention expands the previous capabilities of cardiac electrophysiology mapping systems by providing the ability to map electrophysiology measurements directly to previously obtained three-dimensional images.

The present invention provides the ability to utilize high resolution image data together with electrophysiology measurements taken at the time of treatment. Thus, the present invention permits the blending of different technologies for an improved treatment.

The foregoing and other aspects, features, details, utilities, and advantages of the present invention will be apparent from reading the following description and claims, and from reviewing the accompanying drawings.

Embodiments of the present invention provide a method for mapping electrophysiological information on a three-dimensional model comprising the steps of: A) obtaining a three-dimensional model of at least a portion of a heart comprising position information for a plurality of location points on a surface of the heart; B) obtaining a cardiac electrophysiology map comprising position information for a plurality of measurement points and electrophysiology measurements made at each of the plurality of measurement points; C) choosing a location point from the plurality of location points in the three-dimensional model and determining the two closest measurement points from the cardiac electrophysiology map; D) defining a Delaunay edge between the two measurement points determined to be closest to the chosen location point; repeating steps C) and D) for each of the plurality of location points in the three-dimensional model, to define a plurality of Delaunay edges connecting at least some of the plurality of measurement points within the cardiac electrophysiology map; F) connecting the Delaunay edges to form a plurality of triangles; and G) identifying one of the plurality of location points from the three dimensional model, identifying one of the plurality of triangles whose edges surround the identified location point, and assigning an electrophysiology level to the identified location point based on interpolation using the electrophysiology measurements measured at each of the vertices of the identified triangle.

The methods further optionally include assigning a color or grayscale to each individual location point of a plurality of location points in the three-dimensional model based on a relative magnitude of the electrophysiology level assigned to the individual location point, and presenting the three-dimensional model using the colors assigned to the plurality of location points in the three-dimensional model, in the instance where electrophysiology levels have been assigned to a plurality of location points.

Optionally, the step of obtaining a cardiac electrophysiology map further includes inserting an electrode within a portion of a heart; placing the electrode at a plurality of measurement points along a surface of the heart; receiving position information for each of the plurality of measurement points along a surface of the heart; receiving electrophysiology measurements at each of the plurality of measurement points; and associating the electrophysiology measurements with the respective measurement points at which the electrophysiology measurements were measured.

Optionally, the step of obtaining a three-dimensional model of at least a portion of a heart further includes inserting an electrode within a portion of a heart; placing the electrode at a plurality of location points along a surface of the heart; receiving position information for each of the plurality of location points along a surface of the heart; and generating a three-dimensional model of at least a portion of a heart comprising position information for each of the plurality of location points along the surface of the heart.

Optionally, the step of obtaining a three-dimensional model of at least a portion of a heart further includes inserting an electrode within a portion of a heart; placing the electrode at a first plurality of location points along a surface of the heart; receiving position information for each of the first plurality of location points along a surface of the heart; generating a preliminary three-dimensional geometry of the at least a portion of the heart comprising position information for each of the first plurality of location points along the surface of the heart; and processing the preliminary three-dimensional geometry to create a three-dimensional model comprising position information for each of a second plurality of location points, wherein the second plurality includes at least some of the location points from the first plurality of location points.

Optionally, the step of processing the preliminary three-dimensional geometry to create a three-dimensional model may include processing the preliminary three-dimensional geometry to create a three-dimensional model having position information for each of a second plurality of location points, wherein the three-dimensional model has a finer resolution than the preliminary three-dimensional geometry such that the second plurality of location points is greater in number than the first plurality of location points. The step of processing the preliminary three-dimensional geometry may also include processing the preliminary three-dimensional geometry with a smoothing algorithm to create a three-dimensional model having position information for each of a second plurality of location points. The three-dimensional model may be created using technology including CT scan, MRI, radar imaging, x-ray imaging, fluoroscopic imaging, infrared imaging, ultrasonic imaging, and combinations thereof.

Optionally, the step of choosing a location point from the plurality of location points in the three-dimensional model and determining the two closest measurement points from the cardiac electrophysiology map may further include choosing a location point from the plurality of location points in the three-dimensional model, and using a Kirsanov-Hoppe geodesic algorithm to determine the two measurement points in the cardiac electrophysiology map that are closest in distance to the chosen location point. Additionally, the step of connecting the Delaunay edges into triangles may further include creating additional triangles using measurement points that are not already connected to a Delaunay edge.

Optionally, the step of choosing a location point from the plurality of location points in the three-dimensional model and determining the two closest measurement points from the cardiac electrophysiology map may include choosing a location point from the plurality of location points in the three-dimensional model, and using a Fast Marching geodesic algorithm to determine the two measurement points in the cardiac electrophysiology map that are closest in distance to the chosen location point.

According to another embodiment of the present invention, a method for mapping electrophysiological information on a three-dimensional model is provided comprising the following steps: A) obtaining a three-dimensional model of at least a portion of a heart comprising position information for a plurality of location points on a surface of the heart; B) obtaining a cardiac electrophysiology map comprising position information for a plurality of measurement points and electrophysiology measurements made at each of the plurality of measurement points; C) choosing a location point from the plurality of location points in the three-dimensional model and determining two measurement points from the cardiac electrophysiology map that are closest to the chosen location point; D) defining a Delaunay edge between the two measurement points determined to be closest to the chosen location point; E) repeating steps C) and D) for each of the plurality of location points in the plurality of location points, to define a plurality of Delaunay edges connecting at least some of the plurality of measurement points within the cardiac electrophysiology map; F) connecting the Delaunay edges into triangles to create a triangulated model, and filling any gaps in the triangulated model with new triangles; G) identifying at least one location point that is closer to a measurement point than to any point on the nearest Delaunay edge, and assigning an electrophysiology level to the at least one location point where the assigned electrophysiology level is the same as the electrophysiology measurements measured at the measurement point; and H) assigning an electrophysiology level to at least one location point located inside a triangle, based on interpolation, e.g., barycentric interpolation, using the electrophysiology measurements measured at each of the vertices of the triangle.

According to yet another embodiment of the present invention, a system for mapping electrophysiological information on a three-dimensional model includes: a modeling processor to generate a three-dimensional model of at least a portion of a heart comprising position information for a plurality of location points on a surface of the heart; an electrophysiology measurement device for generating a cardiac electrophysiology map comprising position information for a plurality of measurement points and electrophysiology measurements made at each of the plurality of measurement points, the electrophysiology measurements being associated with the respective measurement points at which the electrophysiology measurements were measured; a Delaunay edge processor to process a subset of the plurality of location points in the three-dimensional model and to determine, for each location point being processed, the two measurement points in the cardiac electrophysiology map that are closest in distance to location point being processed, said processor defining a plurality of Delaunay edges, each of which comprises the pairs of measurement points determined to be closest to each of the location points being processed; a triangulation processor to define a plurality of triangles within the cardiac electrophysiology map based on the plurality of Delaunay edges; and a projection processor to assign an electrophysiology level to at least one location point located within one of the plurality of triangles based on interpolation using the electrophysiology measurements associated with each of the vertices of the triangle.

Optionally, the processor assigns an electrophysiology level to at least one location point that is located within a proximity threshold of a Delaunay edge based on bilinear interpolation using the electrophysiology measurements measured at endpoints of the Delaunay edge.

Optionally, the processor also assigns an electrophysiology level to at least one location point based on the electrophysiology measurements measured at a measurement point that is within a proximity threshold, wherein the electrophysiology level being assigned is the same as that of the measurement point.

According to another embodiment of the present invention a method for mapping electrophysiological information on a three-dimensional model is provided comprising the following steps: A) obtaining a three-dimensional model of at least a portion of a heart comprising position information for a plurality of location points on a surface of the heart; B) obtaining a cardiac electrophysiology map comprising position information for a plurality of measurement points and electrophysiology measurements made at each of the plurality of measurement points; C) choosing a location point from the plurality of location points in the three-dimensional model and determining the two closest measurement points from the cardiac electrophysiology map; D) defining an edge between the two measurement points determined to be closest to the chosen location point; E) repeating steps C) and D) for each of the plurality of location points in the three-dimensional model, to define a plurality of edges connecting at least some of the plurality of measurement points within the cardiac electrophysiology map; F) connecting the edges to form a plurality of polygons; and G) identifying one of the plurality of location points from the three dimensional model, identifying one of the plurality of polygons whose edges surround the identified location point, and assigning an electrophysiology level to the identified location point based on interpolation using the electrophysiology measurements measured at each of the vertices of the identified polygon.

According to yet another embodiment of the present invention, a system for mapping electrophysiological information on a three-dimensional model is providing comprising a surface modeling controller to obtain a three-dimensional model of at least a portion of a heart comprising position information for a plurality of location points on a surface of the heart; an electrophysiology measurement device for generating a cardiac electrophysiology map comprising position information for a plurality of measurement points and electrophysiology measurements made at each of the plurality of measurement points, said electrophysiology measurements being associated with the respective measurement points at which the electrophysiology measurements were measured; an edge processor to process a subset of the plurality of location points in the three-dimensional model and to determine, for each location point being processed, the two measurement points in the cardiac electrophysiology map that are closest in distance to location point being processed, said processor defining a plurality of edges, each of which comprises the pairs of measurement points determined to be closest to each of the location points being processed; a geometry processor to define a plurality of polygons within the cardiac electrophysiology map based on the plurality of edges; and a mapping projector to assign an electrophysiology level to at least one location point located within one of the plurality of polygons based on interpolation using the electrophysiology measurements associated with each of the vertices of the polygons.

Optionally, the processor also assigns an electrophysiology level to at least one location point located near an edge based on bilinear interpolation using the electrophysiology measurements measured at endpoints of the edge.

Optionally, the geometry processor defines the cardiac electrophysiology map using a plurality of triangles. The mapping projector assigns an electrophysiology level to at least one location point located within one of the triangles based on interpolation using the electrophysiology measurements associated with each of the vertices of the triangle.

Yet another embodiment of the present invention provides a computerized method for mapping electrophysiological information on a three-dimensional model comprising the following steps: A) receiving a three-dimensional model of at least a portion of an anatomy comprising position information for a plurality of location points on a surface of the anatomy; B) receiving an electrophysiology map for the anatomy comprising position information for a plurality of measurement points and electrophysiology measurements made at each of the plurality of measurement points; C) using a computer to determine, for each individual location point of the plurality of location points in the three-dimensional model, the two measurement points from the electrophysiology map that are closest to the individual location point and then defining an edge comprising the determined pair of measurement points; D) using the computer to connecting the edges to form a mesh of closed polygons; E) using the computer to identify location points from the three dimensional model that lie on a surface of a closed polygons whose edges surround the identified location point, wherein the computer assigning an electrophysiology level to the identified location point based on interpolation using the electrophysiology measurements measured at each of the vertices of the polygons whose edges surround the identified location point; and F) outputting an output file comprising position information for a plurality of location points and electrophysiology levels that were assigned to each of the plurality of location points.

In accordance with another embodiment of the present invention, a method for mapping electrophysiological information on a three-dimensional model is provided comprising the following steps: A) obtaining a three-dimensional model of at least a portion of a heart comprising position information for a plurality of location points on a surface of the heart; B) obtaining a cardiac electrophysiology map comprising position information for a plurality of measurement points and electrophysiology measurements made at each of the plurality of measurement points; C) processing the three-dimensional model using triangulation so as to create a subdivided three-dimensional model comprising a plurality of triangles in which each of the plurality of measurement points are vertices; and D) processing the subdivided three-dimensional model using a decimation algorithm to generate a revised three-dimensional model comprising a second plurality of triangles, wherein each of the plurality of measurement points is a vertex for a triangle.

Optionally, the triangulation processing step is programmed to disallow the creation of triangular edges which are longer than a predetermined distance threshold.

This embodiment may further include the step of projecting the electrophysiology measurements for a measurement point upon a vertex or edge of the subdivided three-dimensional model using a Kirsanov-Hoppe or Fast Marching geodesic algorithm.

Optionally, this embodiment may further include the step of assigning a color or grayscale to each vertex of the revised three-dimensional model based on a relative magnitude of the electrophysiology level assigned; and presenting the revised three-dimensional model using the colors assigned to the plurality of vertices in the revised three-dimensional model.

DETAILED DESCRIPTION OF THE INVENTION

Figure 1:
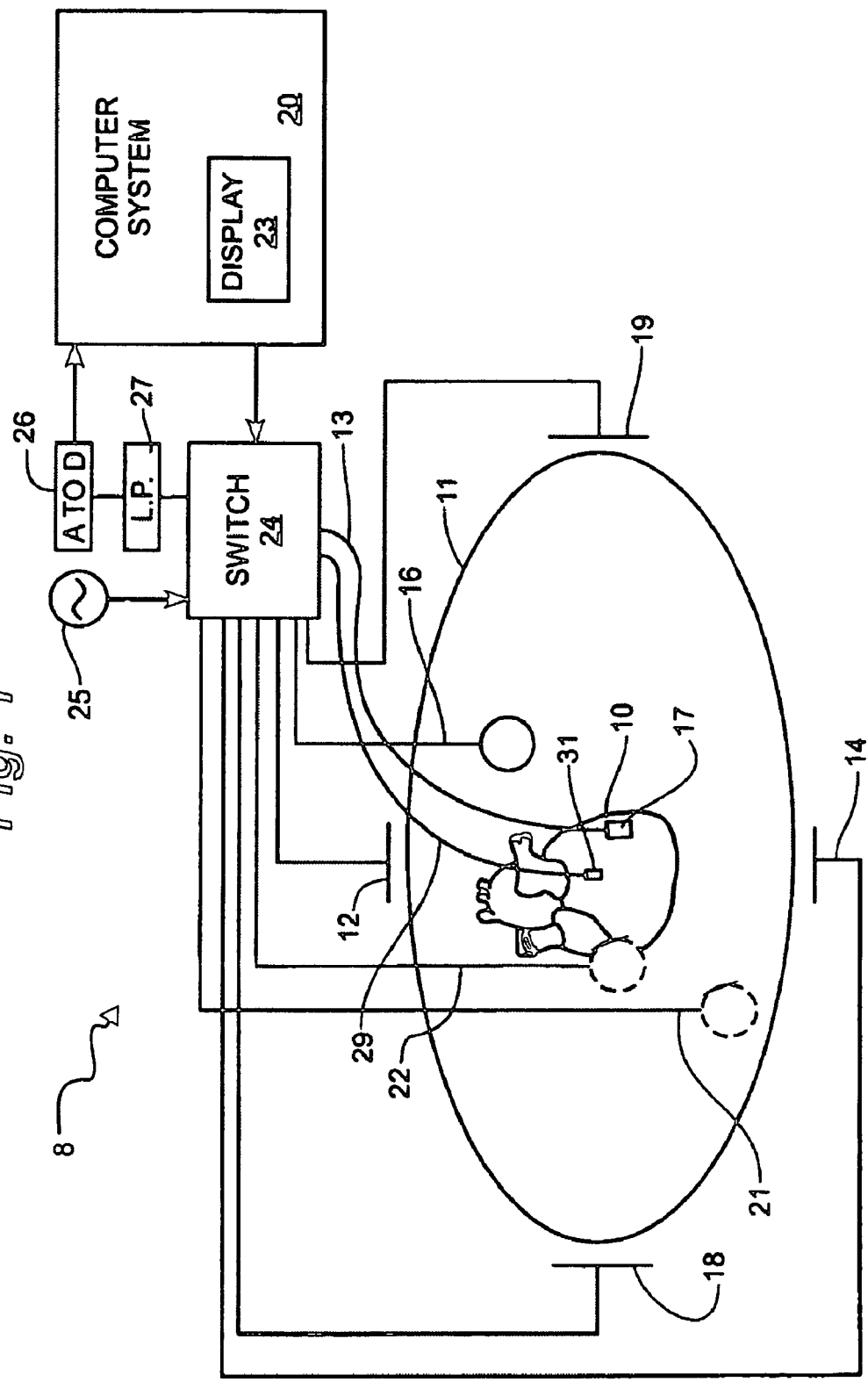
FIG. 1 is a schematic diagram of a system for performing a cardiac electrophysiology examination or ablation procedure wherein the location of one or more electrodes can be determined and recorded.

The present invention improves a system's ability to create an improved electrophysiology mapping of an anatomy. The present invention is not limited to creating accurate models of the heart, but for illustrative purposes, reference will often be made herein to a navigation and localization system used for assessment and treatment of cardiac tissue. The methodology described herein would be equally applicable to modeling other parts of the human anatomy. For purposes of illustrating the present invention, the techniques for creating an electrophysiology map of a cardiac tissue will be described below.

Many conventional systems exist for generating a three-dimensional model of the heart, including systems that utilize technology such as CT scanning, MRI, ultrasound imaging, radar imaging, x-ray imaging, and fluoroscopic imaging. The output of such data may be a plurality of x-y-z data coordinates, spherical coordinates and/or other formats to provide a three-dimensional image. Such imaging technology is often useful in diagnosis as well as preparing for a patient's treatment and/or surgery. Sometimes, the imaging process is performed hours before and in some cases days in advance of the treatment and/or surgery.

Of course, the three-dimensional model may utilize a segmented approach, including for example, a segmented CT or MRI scan image. A segmented model indicates that a subregion of a three-dimensional image has been digitally separated from a larger three-dimensional image, e.g., an image of the right atrium separated from the rest of the heart. Other methodologies and techniques for creating a three-dimensional model of a portion of the patient may also be utilized in accordance with the present invention, including for example, the methodologies and techniques disclosed in U.S. Pat. No. 6,728,562 ("the '562 patent"), the content of which is hereby incorporated by reference in its entirety.

Still other techniques to create a three-dimensional model of the anatomy will be discussed further below.

Techniques available to develop an electrophysiology map will now be discussed in connection with FIG. 1, which shows a schematic diagram of a localization system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity. System 8 can be used to help create an anatomical model using one or more electrodes. System 8 can also be used to measure electrophysiology data at a plurality of points along a cardiac surface, and store the measured data in association with location information for each measurement point at which the electrophysiology data was measured.

The patient 11 is depicted schematically as an oval for simplicity. Three sets of surface electrodes (e.g., patch electrodes) are shown applied to a surface of the patient 11 along an X-axis, a Y-axis, and a Z-axis. The X-axis surface electrodes 12, 14 are applied to the patient along a first axis, such as on the lateral sides of the thorax region of the patient (e.g., applied to the patient's skin underneath each arm) and may be referred to as the Left and Right electrodes. The Y-axis electrodes 18, 19 are applied to the patient along a second axis generally orthogonal to the X-axis, such as along the inner thigh and neck regions of the patient, and may be referred to as the Left Leg and Neck electrodes. The Z-axis electrodes 16, 22 are applied along a third axis generally orthogonal to the X-axis and the Y-axis, such as along the sternum and spine of the patient in the thorax region and may be referred to as the Chest and Back electrodes. The heart 10 lies between these pairs of surface electrodes. An additional surface reference electrode (e.g., a "belly patch") 21 provides a reference and/or ground electrode for the system 8. The belly patch electrode 21 is an alternative to a fixed intra-cardiac electrode 31. It should also be appreciated that, in addition, the patient 11 will have most or all of the conventional electrocardiogram (ECG) system leads in place. This ECG information is available to the system 8 although not illustrated in the FIG. 1.

In a preferred embodiment, the localization/mapping system is the EnSite NavX™ navigation and visualization system of St. Jude Medical, Atrial Fibrillation Division, Inc. Other localization systems, however, may be used in connection with the present invention, including for example, the CARTO navigational and location system of Biosense Webster, Inc. and the LOCALISA intracardiac navigation system of Medtronic, Inc. The localization and mapping systems described in the following patents (all of which are hereby incorporated by reference in their entireties) can be used with the present invention: U.S. Pat. Nos. 6,990,370; 6,978,168; 6,947,785; 6,939,309; 6,728,562; 6,640,119; 5,983,126; and 5,697,377.

A representative catheter 13 having at least one electrode 17 (e.g., a distal electrode) is also shown. This representative catheter electrode 17 is referred to as the "roving electrode" or "measurement electrode" throughout the specification. Typically, multiple electrodes on catheter 13, or on multiple such catheters, will be used. In one embodiment, for example, the system 8 may comprise up to sixty-four electrodes on up to twelve catheters disposed within the heart and/or vasculature of the patient. Of course, this embodiment is merely exemplary, and any number of electrodes and catheters may be used within the scope of the present invention.

An optional fixed reference electrode 31 (e.g., attached to a wall of the heart 10) is also shown on a second catheter 29. For calibration purposes, this electrode 31 may be stationary (e.g., attached to or near the wall of the heart) or disposed in a fixed spatial relationship with the roving electrode 17. The fixed reference electrode 31 may be used in addition or alternatively to the surface reference electrode 21 described above. In many instances, a coronary sinus electrode or other fixed electrode in the heart 10 can be used as a reference for measuring voltages and displacements.

Each surface electrode is coupled to the multiplex switch 24 and the pairs of electrodes are selected by software running on a computer 20, which couples the electrodes to a signal generator 25. The computer 20, for example, may comprise a conventional general-purpose computer, a special-purpose computer, a distributed computer, or any other type of computer. The computer 20 may comprise one or more processors, such as a single central-processing unit, or a plurality of processing units, commonly referred to as a parallel processing environment.

Generally, three nominally orthogonal electric fields are generated by a series of driven and sensed electric dipoles in order to realize catheter navigation in a biological conductor. Alternately, these orthogonal fields can be decomposed and any pairs of surface electrodes can be driven as dipoles to provide effective electrode triangulation. Additionally, such nonorthogonal methodologies add to the flexibility of the system. For any desired axis, the potentials measured across an intra-cardiac electrode 17 resulting from a predetermined set of drive (source-sink) configurations are combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, e.g., the belly patch 21, while the unexcited electrodes measure voltage with respect to the ground reference. The measurement electrode 17 placed in the heart 10 is exposed to the field from a current pulse and is measured with respect to ground, e.g., the belly patch 21. In practice the catheters within the heart may contain multiple electrodes and each electrode potential may be measured. As previously noted, at least one electrode may be fixed to the interior surface of the heart to form a fixed reference electrode 31, which is also measured with respect to ground. Data sets from each of the surface electrodes, the internal electrodes, and the virtual electrodes may all be used to determine the location of the measurement electrode 17 or other electrodes within the heart 10.

One of skill in the art will readily appreciate that the measurement electrode 17 can also be used to measure electrophysiology data and system 8 can be used to store the electrophysiology data (e.g., voltage readings, including without limitation, voltage variations over a period of time) in association with location information for the measurement point at which the electrophysiology data was measured.

For example, all of the raw electrode voltage data is measured by the A/D converter 26 and stored by the computer 20 under the direction of software. This electrode excitation process occurs rapidly and sequentially as alternate sets of surface electrodes are selected and the remaining non-driven electrodes are used to measure voltages. This collection of voltage measurements is referred to herein as the "electrode data set." The software has access to each individual voltage measurement made at each electrode during each excitation of each pair of surface electrodes.

The raw electrode data is used to determine the "base" location in three-dimensional space (X, Y, Z) of the electrodes inside the heart, such as the roving electrode 17, and any number of other electrodes located in or around the heart and/or vasculature of the patient 11. FIG. 2 shows a catheter 13, which may be a conventional electrophysiology catheter (sometimes referred to as an "EP catheter"), extending into the heart 10. In FIG. 2, the catheter 13 extends into the left ventricle 50 of the heart 10. The catheter 13 comprises the distal electrode 17 discussed above with respect to FIG. 1 and has additional electrodes 52, 54, and 56. Since each of these electrodes lies within the patient (e.g., in the left ventricle of the heart), location data may be collected simultaneously for each of the electrodes. In addition, when the electrodes are disposed adjacent to the surface, although not necessarily directly on the surface of the heart, and when the current source 25 is "off" (i.e., when none of the surface electrode pairs is energized), at least one of the electrodes 17, 52, 54, and 56 can be used to measure electrical activity (e.g., voltage) on the surface of the heart 10.

The data used to determine the location of the electrode(s) within the heart is measured while the surface electrode pairs impress an electric field on the heart. A number of electrode locations may be collected by either sampling a number (e.g., sixty-two electrodes spread among up to twelve catheters) simultaneously or in sequence (e.g., multiplexed) and/or by sampling one or more electrodes (e.g., the roving electrode 17) being moved within the patient (e.g., a chamber of the heart). In one embodiment, the location data for individual electrodes are sampled simultaneously, which allows for collection of data at a single stage or phase of a heartbeat. In another embodiment, location data may be collected either synchronously with one or more phases of the heartbeat or without regard for any particular stage of the heartbeat. Where the data is collected across the phases of the heartbeat, data corresponding to locations along the wall of the heart will vary with time. In one variation, the data corresponding to the outer or inner locations may be used to determine the position of the heart wall at the maximum and minimum volumes, respectively. For example, by selecting the most exterior points it is possible to create a "shell" representing the shape of the heart at its greatest volume.

The electrode data may also be used to create a respiration compensation value used to improve the raw location data for the electrode locations as described in U.S. Patent Application Publication No. 2004/0254437, which is hereby incorporated herein by reference in its entirety. The electrode data may also be used to compensate for changes in the impedance of the body of the patient as described in co-pending U.S. patent application Ser. No. 11/227,580, filed on 15 Sep. 2005, which is also incorporated herein by reference in its entirety.

In summary, the system 8 first selects a set of surface electrodes and then drives them with current pulses. While the current pulses are being delivered, electrical activity, such as the voltages measured at least one of the remaining surface electrodes and in vivo electrodes are measured and stored. At this point, compensation for artifacts, such as respiration and/or impedance shifting may be performed as indicated above. As described above, various location data points are collected by the system 8 that are associated with multiple electrode locations (e.g., endocardial electrode locations). Each point in the set has coordinates in space. In one embodiment, the system 8 collects location data points for up to sixty-four electrodes that may be located on up to twelve catheters simultaneously or in close proximity to one another. However, smaller or larger data sets may be collected and result in less complex and lower resolution or more complex and higher resolution representations of the heart, respectively.

A three-dimensional model of a portion of the patient, e.g., a region of the patient's heart or surrounding vasculature, may be created from the location data points, e.g., during the same or a previous procedure, or a previously generated three-dimensional model, e.g., a segmented CT or MRI scan image, may be used. A segmented model indicates that a subregion of a three-dimensional image has been digitally separated from a larger three-dimensional image, e.g., an image of the right atrium separated from the rest of the heart. Exemplary segmentation applications include ANALYZE (Mayo, Minneapolis, Minn.), Verismo (St. Jude Medical, Inc., St. Paul, Minn.), and CardEP (General Electric Medical Systems, Milwaukee, Wis.). Where the three-dimensional model is created from the location data points collected by the system 8, for example, during a single procedure by sweeping one or more electrodes over the surface of the heart, the exterior-most location points in the data can be used to determine a shape corresponding to the volume of a region of the patient's heart.

Other methodologies and techniques for creating three-dimensional models of a portion of the patient may also be utilized in accordance with the present invention. For example, a convex hull may be generated using standard algorithms such as the Qhull algorithm. The Qhull algorithm, for example, is described in Barber, C. B., Dobkin, D. P., and Huhdanpaa, H. T., "The Quickhull algorithm for convex hulls," *ACM Trans. on Mathematical Software,* 22(4):469-483, December 1996. Other algorithms used to compute a convex hull shape are known and may also be suitable for use in implementing the invention. This surface may then be re-sampled over a more uniform grid and may be interpolated to give a reasonably smooth surface stored as a three-dimensional model for presentation to the physician during the same or a later procedure. The re-sampled surface generally may have a greater number of data points. The re-sampled surface may also be processed using a smoothing algorithm, which will give the geometry a much smoother appearance. Such a three-dimensional model, for example, provides an estimated boundary of the interior of the heart region from the set of points.

Figure 3:
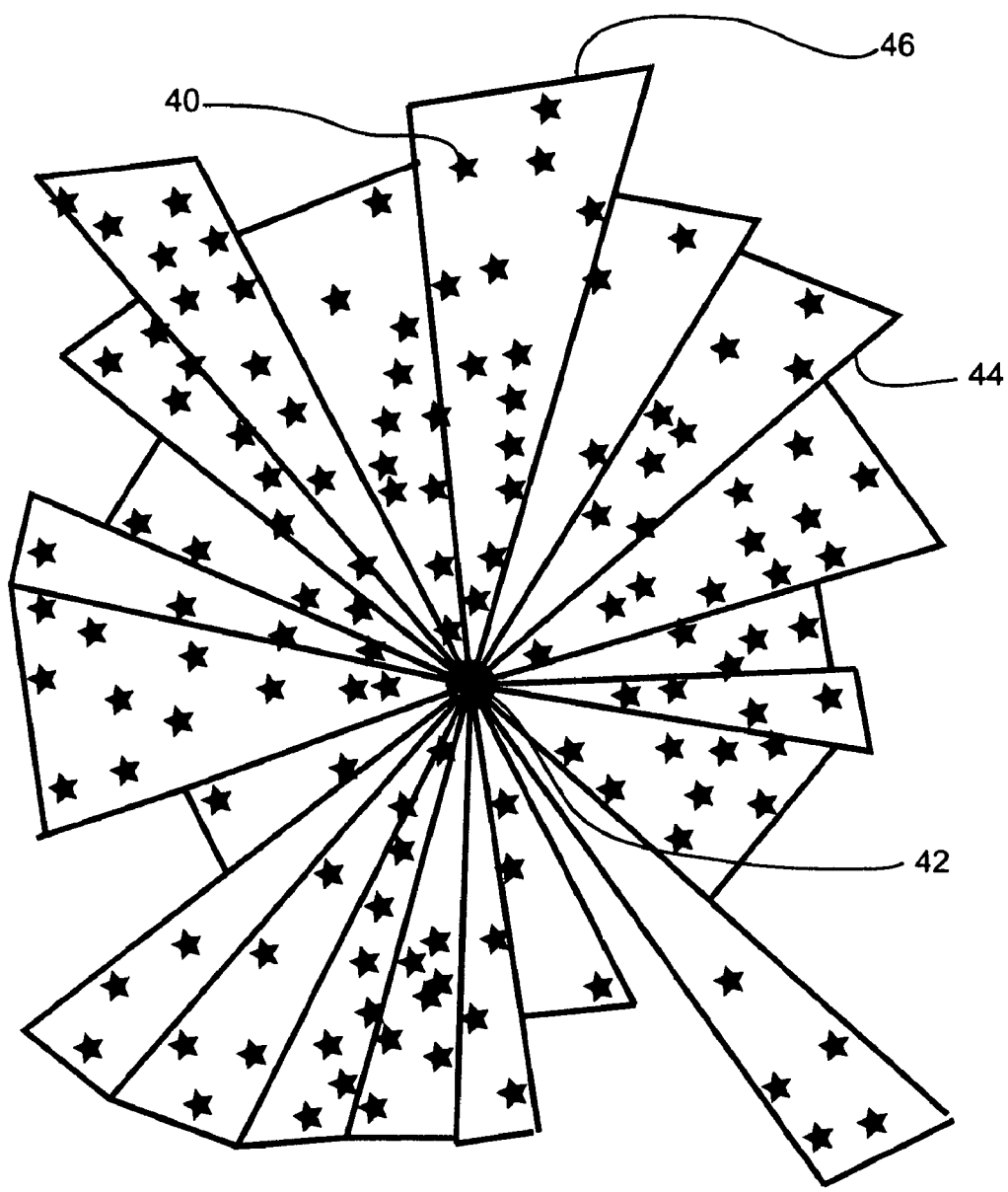
FIG. 3 is a schematic diagram of an exemplary methodology for rendering a surface of a heart cavity using recorded electrode position data points.

FIG. 3 schematically depicts another exemplary method for creating a shell corresponding to the shape of a heart chamber. The location data identifying position data points 40 of one or more electrodes within the heart chamber over a period of time is accessed. The location data may be represented as a cloud of points within the heart chamber. The most distant position data points 40 will thus correspond to the interior wall of the heart chamber in a relaxed or diastole state corresponding to its greatest volume. A shell or surface is rendered from this location data by fitting an array of "bins" 44 around groups of the position data points 40. The bins 44 are constructed by determining a mean center point 42 within the cloud of position data points 40 and then extending borders radially outward from the center point 42. The bins 44 extend to the furthest position data point 40 within the slice encompassed by the bin 44. It should be noted that even though FIG. 3 is schematically presented in two dimensions, the bins 44 are three-dimensional volumes. The radial end faces 46 of the bins 44 thus approximate the surface of the heart chamber wall. Common graphic shading algorithms can then be employed to "smooth" the surface of the shell thus created out of the radial end faces 46 of the bins 44.

Another example of creating a three-dimensional map using a cloud of points is described in U.S. application Ser. No. 11/647,275, filed 29 Dec. 2006. Yet another technique for creating a three-dimensional map of a tissue surface is described in U.S. application Ser. No. 11/647,298, filed 29 Dec. 2006.

Figure 2:
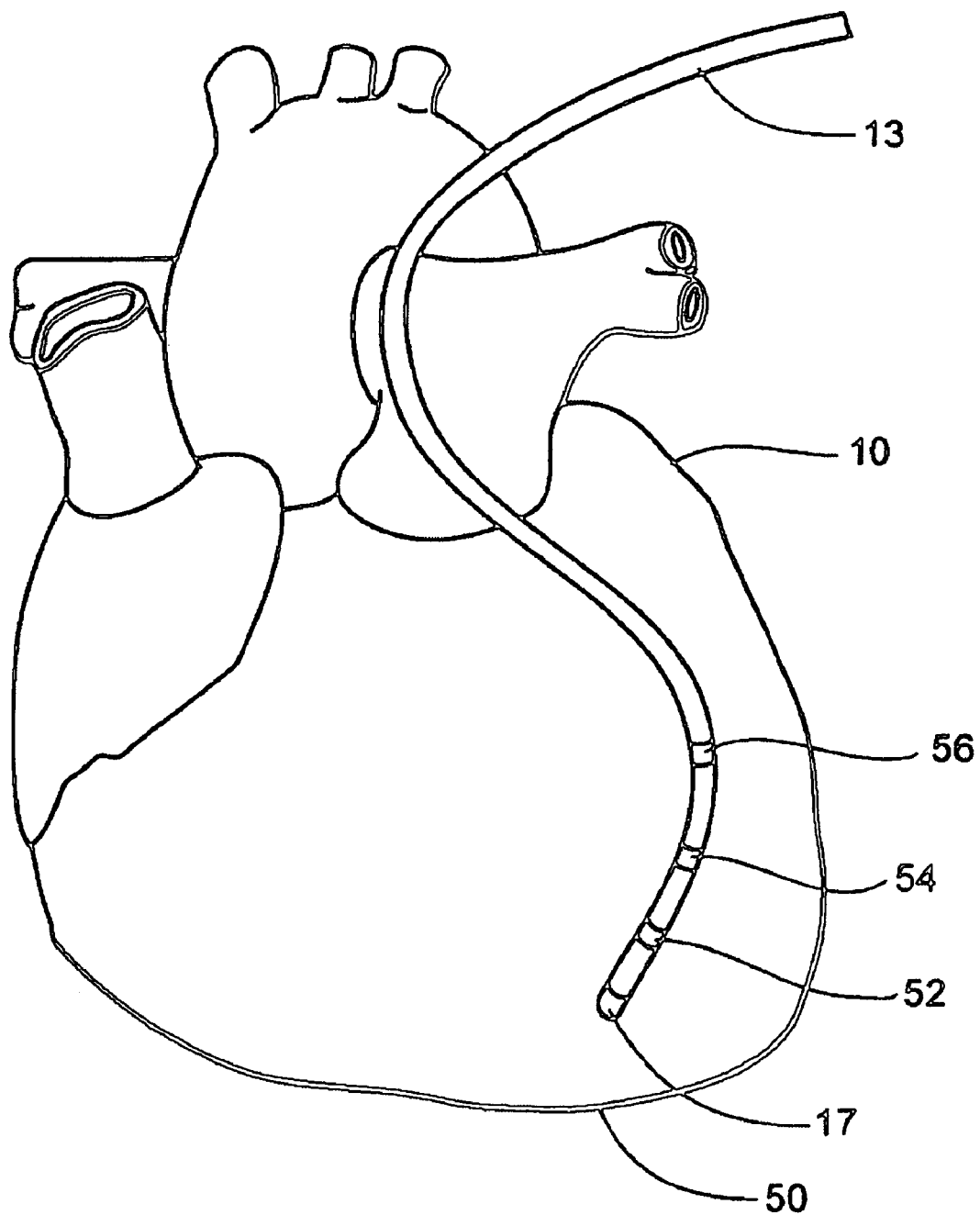
FIG. 2 is a schematic representation of a heart investigated by an electrophysiology catheter with several distal electrodes.
Figure 4:
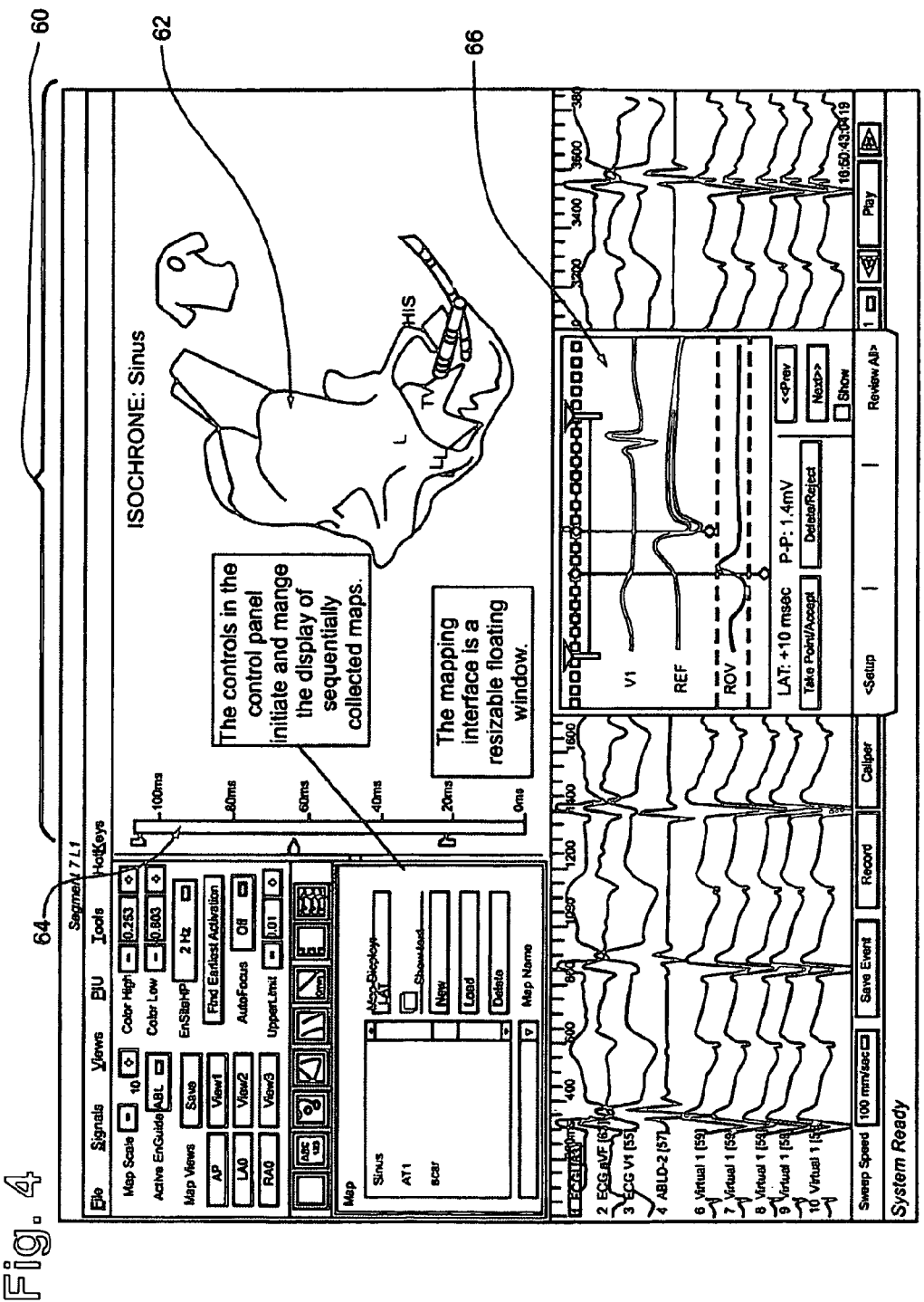
FIG. 4 is a schematic depiction of a graphical user interface for displaying electrocardiograph and related electrophysiological information to a clinician.

Various electrophysiology data may be measured and presented to a cardiologist through the display 23 of the system 8 shown in FIG. 1. FIG. 4 depicts an illustrative computer display that may be displayed via the computer 20. The display 23, for example, may be used to show data to a user, such as a physician, and to present certain options that allow the user to tailor the configuration of the system 8 for a particular use. It should be noted that the contents on the display can be easily modified and the specific data presented is illustrative only and not limiting of the invention. An image panel 60 shows a three-dimensional model of a heart chamber 62 identifying regions that received a depolarization waveform at the same time, i.e., "isochrones," mapped to the model in false color or grayscale. The isochrones are, in one variation, mapped to three-dimensional coordinates (e.g., X, Y, Z) corresponding to the electrogram from which they were obtained. The isochrones are also shown in guide bar 64 as a key, identifying information associated with a particular color or grayscale mapped to the three-dimensional model. In this image, the locations of multiple electrodes on a pair of catheters are also mapped to the three-dimensional model. Other data that may be mapped to the heart surface model include, for example, the magnitude of a measured voltage and the timing relationship of a signal with respect to heartbeat events. Further, the peak-to-peak voltage measured at a particular location on the heart wall may be mapped to show areas of diminished conductivity and may reflect an infarcted region of the heart.

Figure 5:
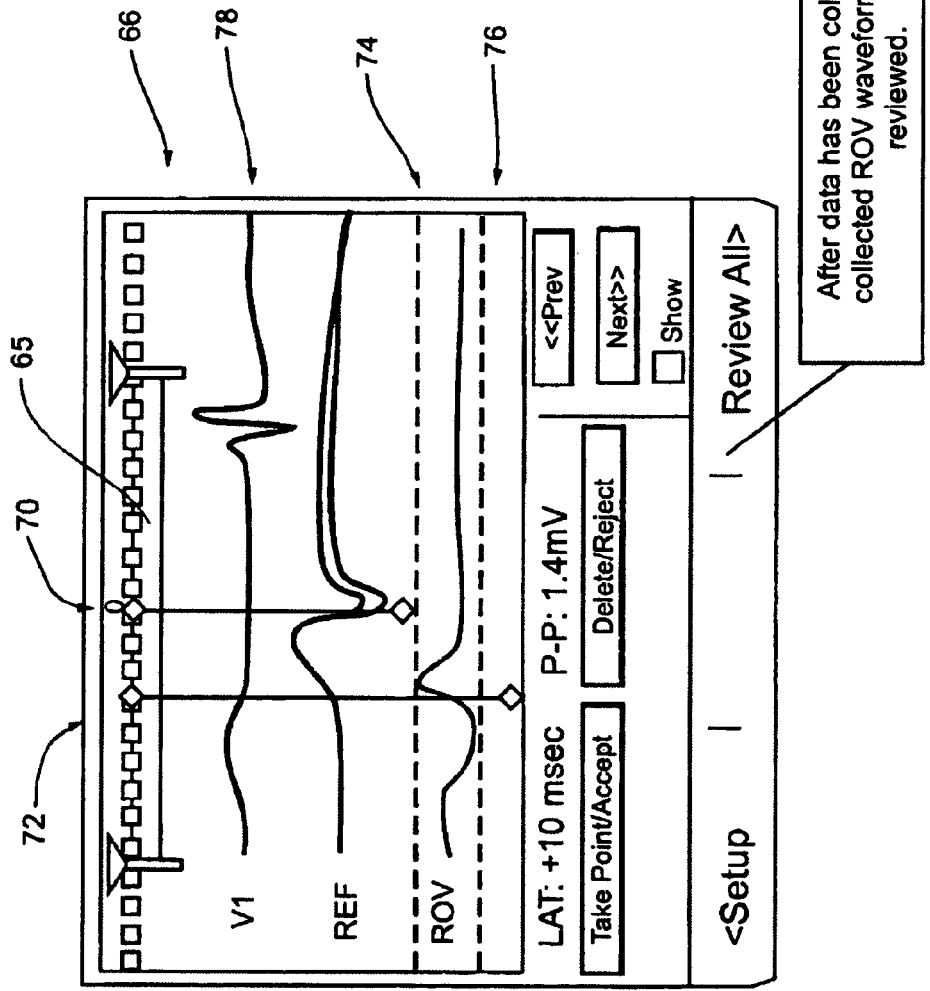
FIG. 5 is an enlargement of the panel 66 depicted in FIG. 4.

In the variation shown in FIG. 4, for example, the guide bar 64 is graduated in milliseconds and shows the assignment of each color or grayscale to a particular time relationship mapped to the three-dimensional model. The relationship between the color or grayscale on the three-dimensional model image 62 and the guide bar 64 can also be determined by a user with reference to the information shown in panel 66. FIG. 5 shows an enlargement of the panel 66 depicted in FIG. 4. The panel 66, in this variation, shows timing information used to generate isochrones mapped on the three-dimensional model 62 shown in FIG. 4. In general, a fiducial point is selected as the "zero" time. In FIG. 5, for example, the inflection point 70 of a voltage appearing on a reference electrode is used as the primary timing point for the creation of isochrones. This voltage may be acquired from either a virtual reference or a physical reference (e.g., the roving electrode 17 shown in FIG. 1). In this variation, the voltage tracing corresponding to the fiducial point is labeled "REF" in FIG. 5. The roving electrode signal is depicted in FIG. 5 and is labeled "ROV." The inflection point 72 of the voltage signal ROV corresponds to the roving electrode 31. The color guide bar 65 shows the assignment of color or grayscale tone for the timing relationship seen between inflection points 70 and 72 of the reference and roving voltage signals REF and ROV, respectively.

The amplitude of the voltage signal ROV corresponding to the roving electrode 17 is also shown on panel 66 of FIG. 5. The amplitude of the time-varying signal ROV is located between two adjustable bands 74 and 76, which can be used to set selection criteria for the peak-to-peak voltage of the signal ROV. In practice, regions of the heart with low peak-to-peak voltage are the result of infarcted tissue, and the ability to convert the peak-to-peak voltage to grayscale or false color allows identification of the regions that are infarcted or ischemic. In addition, a time-varying signal "V1" is also shown and corresponds to a surface reference electrode, such as a conventional ECG surface electrode. The signal V1, for example, may orient a user, such as a physician, to the same events detected on the surface of the patient.

Various time-domain information related to the EP activity in and/or around the heart of a patient may be mapped to the three-dimensional model. For example, the time difference of an action potential measured at a roving electrode and a reference electrode, the peak-to-peak voltage of an action potential measured at the roving electrode, and/or the peak negative voltage of an action potential measured at the roving electrode may be mapped to a three-dimensional model. In one embodiment, EP activity from up to sixty-two roving electrodes may be collected and mapped to the three-dimensional model.

Figure 6:
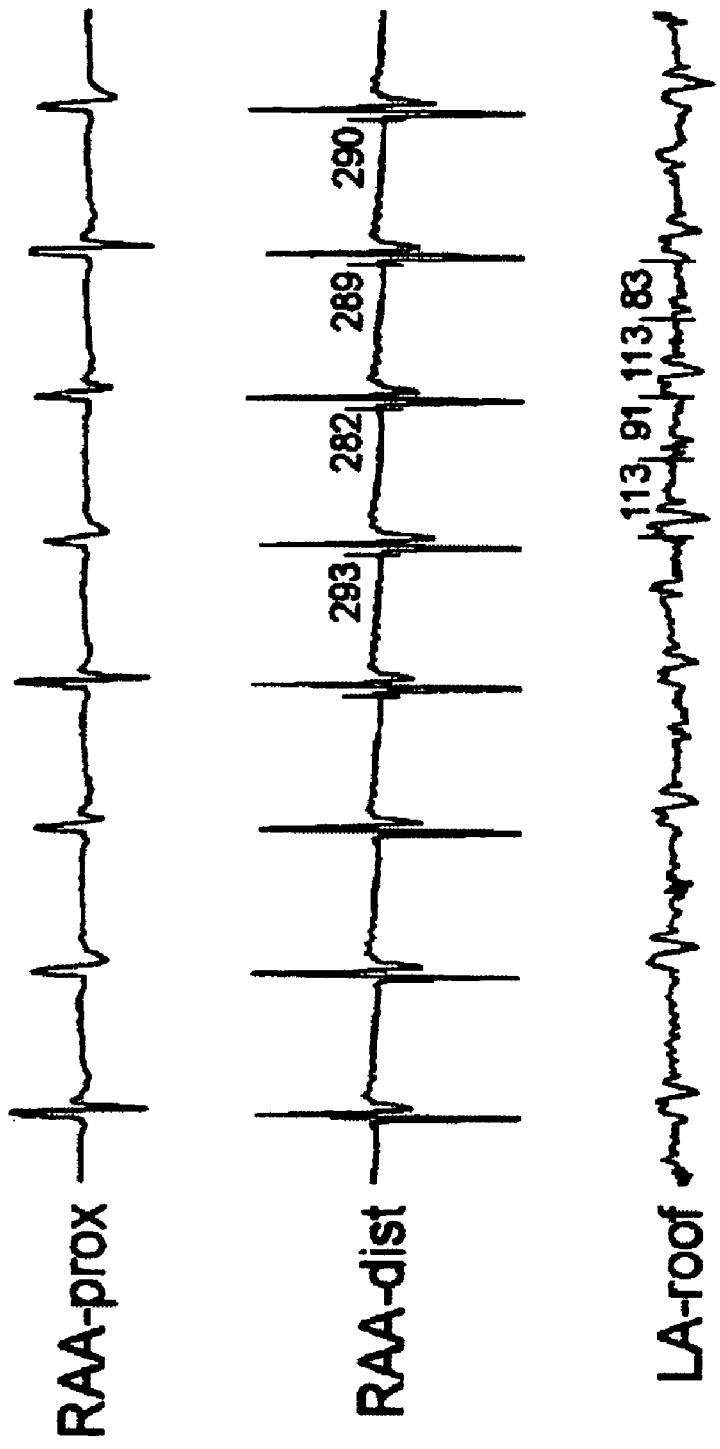
FIG. 6 shows side-by-side views of time-varying electrograms collected for various locations along a wall of a heart.
Figure 7:
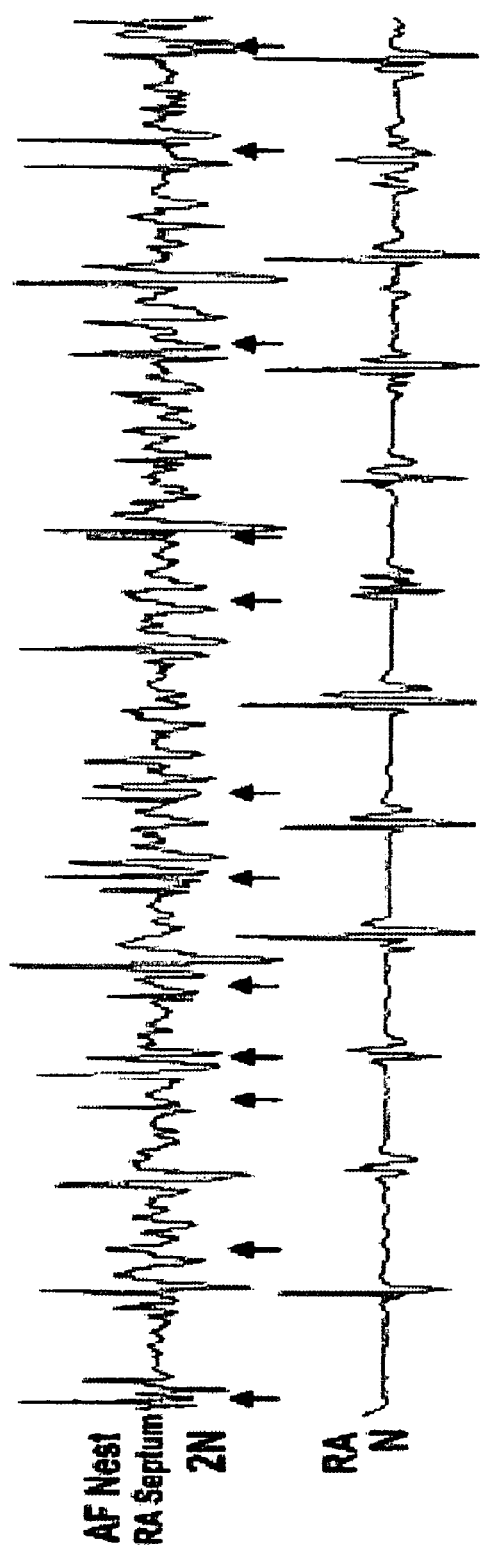
FIG. 7 shows side-by-side views of time-varying electrograms collected for various locations along a wall of a heart.

Complex fractionated electrogram (CFE) and frequency-domain information may also be mapped to the three-dimensional model. CFE information, for example, may be useful to identify and guide ablation targets for atrial fibrillation. CFE information refers to irregular electrical activation (e.g., atrial fibrillation) in which an electrogram comprises at least two discrete deflections and/or perturbation of the baseline of the electrogram with continuous deflection of a prolonged activation complex (e.g., over a 10 second period). Electrograms having very fast and successive activations are, for example, consistent with myocardium having short refractory periods and micro-reentry. FIG. 6, for example, shows a series of electrograms. (FIG. 6 is associated with an article by NADE-MANEE, Koonlawee, M. D., FACC, et. al., *A new approach for catheter ablation of atrial fibrillation: Mapping of the electrophysiologic substrate*, Journal of the American College of Cardiology, (2004) Vol. 43, No. 11, 2044-53.) The first two electrograms, RAA-prox and RAA-dist, comprise typical electrograms from the right atrium of a patient such as from a proximal roving electrode and a distal roving electrode in the right atrium of a patient, respectively. The third electrogram, LA-roof, comprises a CFE electrogram, such as from the roof of the patient's left atrium. In this third electrogram, LA-roof, the cycle lengths indicated by the numbers shown in the electrogram are substantially shorter than the cycle lengths indicated by the numbers shown in the first two electrograms, RAA-prox and RAA-dist. In another example shown in FIG. 7, a first electrogram RA-Septum comprises fast and successive activations indicated by the arrows compared to the second electrogram RA. The fast and successive activations, for example, can be consistent with myocardial tissue having short refractory periods and micro-reentry, e.g., an atrial fibrillation "nest."

The presence of CFE information can be detected from the EP information (e.g., electrograms) collected by an electrode, for example, by monitoring the number of deflections within an electrogram segment; calculating the average time between deflections within an electrogram segment; monitoring the variation of time between deflections within a cycle length of an electrogram; and calculating slopes, derivatives, and amplitudes of electrograms. For example, discrete activations have an associated peak-to-peak value measured over a specified time period. This peak-to-peak value may be used to quantify a discrete activation. As shown in FIG. 5, a time instant of the discrete activations can be marked on the electrogram on the user display. The time instant and/or other quantifications of the fractionation of the electrogram may be used to determine the presence and/or absence of CFE information. The mean interval between discrete activations within a predetermined time period may, for example, be used as an index to quantify the degree of fractionation of a given electrogram. In this example, a value of one may be assigned to the electrogram if there is only one discrete activation within the given time period, and a lesser or higher value may be assigned if more than one discrete activation is present in the given time period. Another quantification may comprise, for example, quantifying the variance in time between discrete activations of an electrogram. These or other quantifications of the time-domain correlate with the morphology of the electrogram and are, in turn, based upon the underlying physiology of the region from which the electrogram was sampled.

In diagnosing atrial fibrillation and guiding an ablation catheter, the electrograms corresponding to physiological mechanisms for initiating and sustaining atrial fibrillation may be identified by quantifying the fractionation of the electrograms. These quantifications, in turn, may be used to identify regions to be ablated to eliminate the atrial fibrillation. Mid-diastolic potentials within an ischemic area of the cardiac chamber may also be identified by quantifying the fractionation of the electrograms collected in a region of the heart. Healthy tissue would correspond to non-fractionated electrograms (i.e., a single discrete activation), while unhealthy tissue (e.g., ischemic tissue) would correspond to fractionated electrograms (i.e., multiple discrete activations and/or perturbations of the baseline). The time instant or other quantifications of CFE information in electrograms may then be mapped to a three-dimensional model as described above.

In addition to and/or alternatively to the time-domain information analyzed and mapped from the collected EP information, frequency-domain information may also be mapped to a three-dimensional model. In one embodiment, for example, a fast Fourier transform (FFT) or other method of translating a time-varying signal into frequency-domain information may be used to translate the collected signal into a frequency-domain. The frequency domain depicts a spectrum that represents the energy or power of frequency components of a time-varying electrogram signal. FFTs and other transforms are known in the art and are not discussed in further detail herein.

Figure 8:
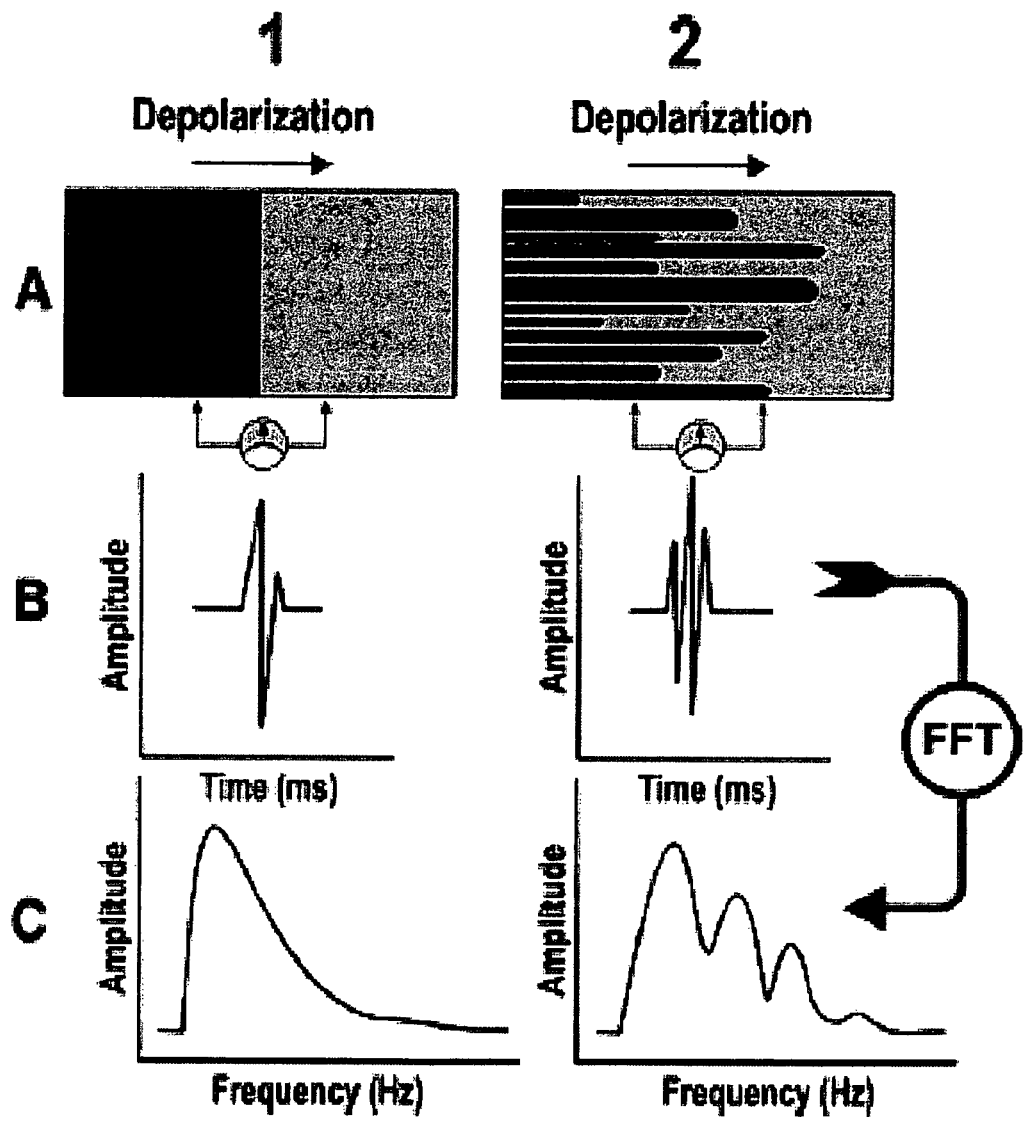
FIG. 8 shows side-by-side comparisons of electrograms for typical compact and fibrillar myocardial muscle tissues in the time-domain and frequency-domain.

FIG. 8 shows a side-by-side comparison of compact myocardial muscle and fibrillar myocardial muscle that together form the wall of the heart. Compact myocardial muscle tissue comprises groups of tightly-connected cells that conduct electrical activity during depolarization of the heart in a homogenous fashion by transmitting electrical activity at equal speeds in any direction. Fibrillar myocardial muscle tissue, however, typically comprises loosely connected cells, such as transitions between neural, vascular, and atrial tissue. Fibrillar myocardial muscle tissue may also be formed by stretching and/or degeneration of cells leading to poor connections between such damaged tissue. In row A, the first column shows the homogenous or uniform activation of compact myocardial muscle tissue during depolarization of the heart wall. In the second column, however, the irregular activation of fibrillar myocardial muscle tissue is shown during depolarization in which a wave travels at different rates through different strands or portions of the fibrillar myocardial muscle tissue, thus causing asynchronous contraction in different portions of the myocardium.

In row B, time-domain electrogram signals are shown for the compact myocardial muscle tissue and the fibrillar myocardial muscle tissue during a depolarization phase of a heartbeat. As shown in FIG. 8, the time-domain electrogram signals typically comprise a biphasic or triphasic shape for compact myocardial muscle tissue (shown in column 1) and a more polyphasic shape for fibrillar myocardial muscle tissue (shown in column 2). Finally, the frequency-domain of the electrogram signals of row B for compact myocardial muscle tissue and fibrillar myocardial muscle tissue is shown in row C. The frequency-domain is obtained by performing an FFT on a time period of the time-varying electrograms shown row B, column 1 for compact myocardial muscle tissue and row B, column 2 for fibrillar myocardial muscle tissue. As shown in row C of FIG. 8, the frequency spectrum for compact myocardial muscle tissue typically comprises a higher amplitude at a single peak located around a fundamental frequency, while the frequency spectrum for the fibrillar myocardial muscle tissue typically comprises a lower amplitude at its fundamental frequency due to a right-shift of the frequency caused by a number of harmonic frequency components.

As shown in FIG. 8, fibrillar myocardial muscle tissue can lead to irregular wavefronts of electrical activity during depolarization of the heart. The greater the ratio of fibrillar myocardial muscle tissue to compact myocardial muscle tissue, the more likely there is a propensity for atrial fibrillation. In such areas "atrial fibrillation nests" (or "AFIB nests") may be identified as potential sources of atrial fibrillation. Thus, by use of frequency-domain information, a physician may be able to further identify potential trouble spots that may lead to atrial fibrillation.

Figure 9A:
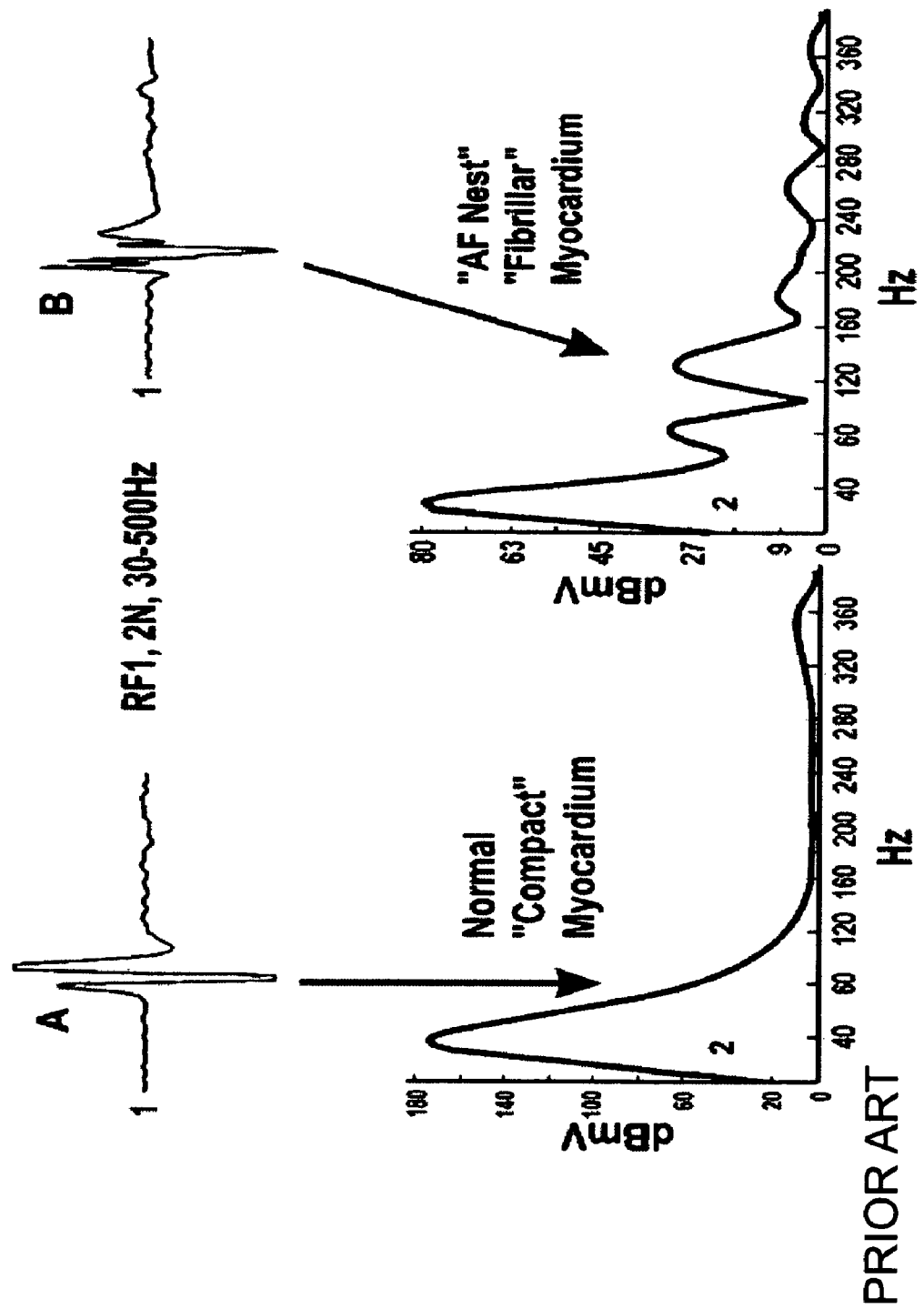
FIG. 9A shows a side-by-side comparison of time-domain and frequency-domain information for electrograms.

Various numerical indices can be obtained from the frequency spectrum of the electrogram signal. Any of these indices can then be mapped to a three-dimensional model of a patient's heart to allow a user such as a physician to identify locations on the wall of the heart that correspond to a particular characteristic. In one exemplary variation of the present invention, a dominant frequency of an electrogram signal can be identified in the frequency spectrum, which has been obtained via a FFT. As can be seen in FIG. 9A, for example, a typical normal, or compact, myocardial muscle tissue may have a single peak in the spectrum, while a fibrillar myocardial muscle tissue has more spectral peaks than does a compact myocardial muscle tissue. The number of spectral peaks may be determined for multiple points around the wall of the heart on a three-dimensional model as described above. (FIGS. 7-9a are associated with an article by PACHON, Jose, C., et. al., *A new treatment for atrial fibrillation based on spectral analysis to guide the catheter RF-ablation*, Europace, (2004) 6, 590-601, The European Society of Cardiology.)

In another variation of the present invention, a maximum peak amplitude at the dominant frequency may be determined from the frequency spectrum of the electrogram signal and may be mapped to a three-dimensional model of the heart. In FIG. 9A, for example, the maximum peak amplitude at the dominant frequency of compact myocardial muscle tissue can be seen to be higher at about 175 dB mV, while the maximum peak amplitude at the dominant frequency of fibrillar myocardial muscle tissue is lower at about 80 dB mV. These values may also be mapped onto a three-dimensional model of the heart.

Figure 9B:
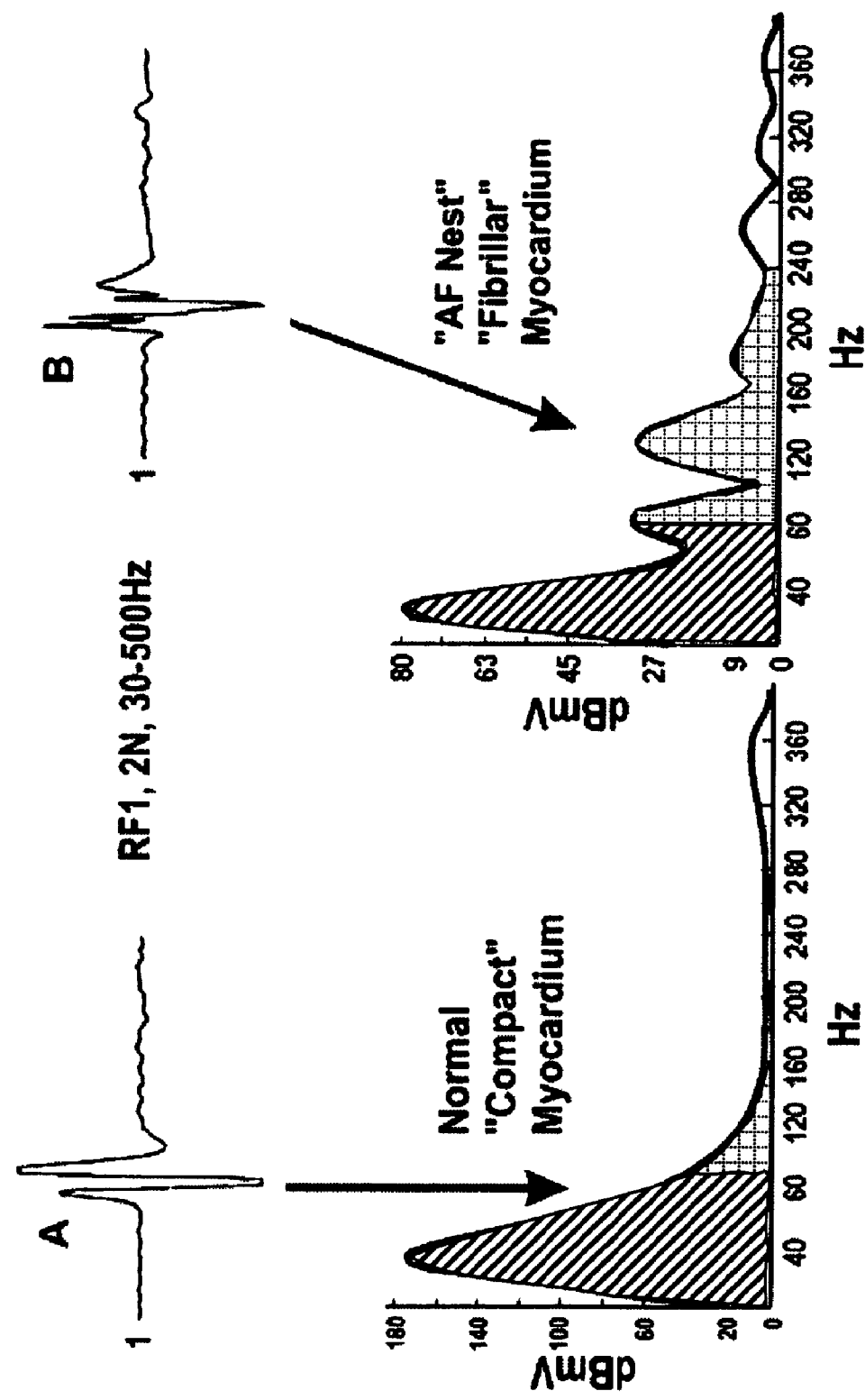
FIG. 9B shows a side-by-side comparison of time-domain and frequency-domain information for electrograms with energy in multiple spectral bands shown in cross-hatch.

In yet another variation, a ratio of energy in one band of the frequency-domain to the energy in a second band of the frequency-domain may be determined and mapped to a three-dimensional model of the heart. For example, FIG. 9B shows the ratio of energy in the passband of 60 to 240 Hz to the energy below 60 Hz is higher for the spectrum of electrograms from fibrillar myocardial muscle tissue than in the spectrum of electrograms from compact myocardial muscle tissue.

While examples of time-domain and frequency-domain information have been described herein as able to be translated to a three-dimensional map of a patient's heart, one skilled in the art would recognize that other time- and frequency-domain information may also be determined and mapped to a three-dimensional model. For example, the following information may be determined from the time-domain or frequency-domain and mapped to a three-dimensional model: a low-frequency or high-frequency passband of interest (e.g., in Hz); a frequency with the maximum energy in a passband (e.g., in Hz); a number of peaks within a passband (e.g., a count); an energy, power, and/or area in each peak (e.g., dB); a ratio of energy and/or area in each peak to that in another passband; and a width of each peak in a spectra (e.g., in Hz).

Figure 10:
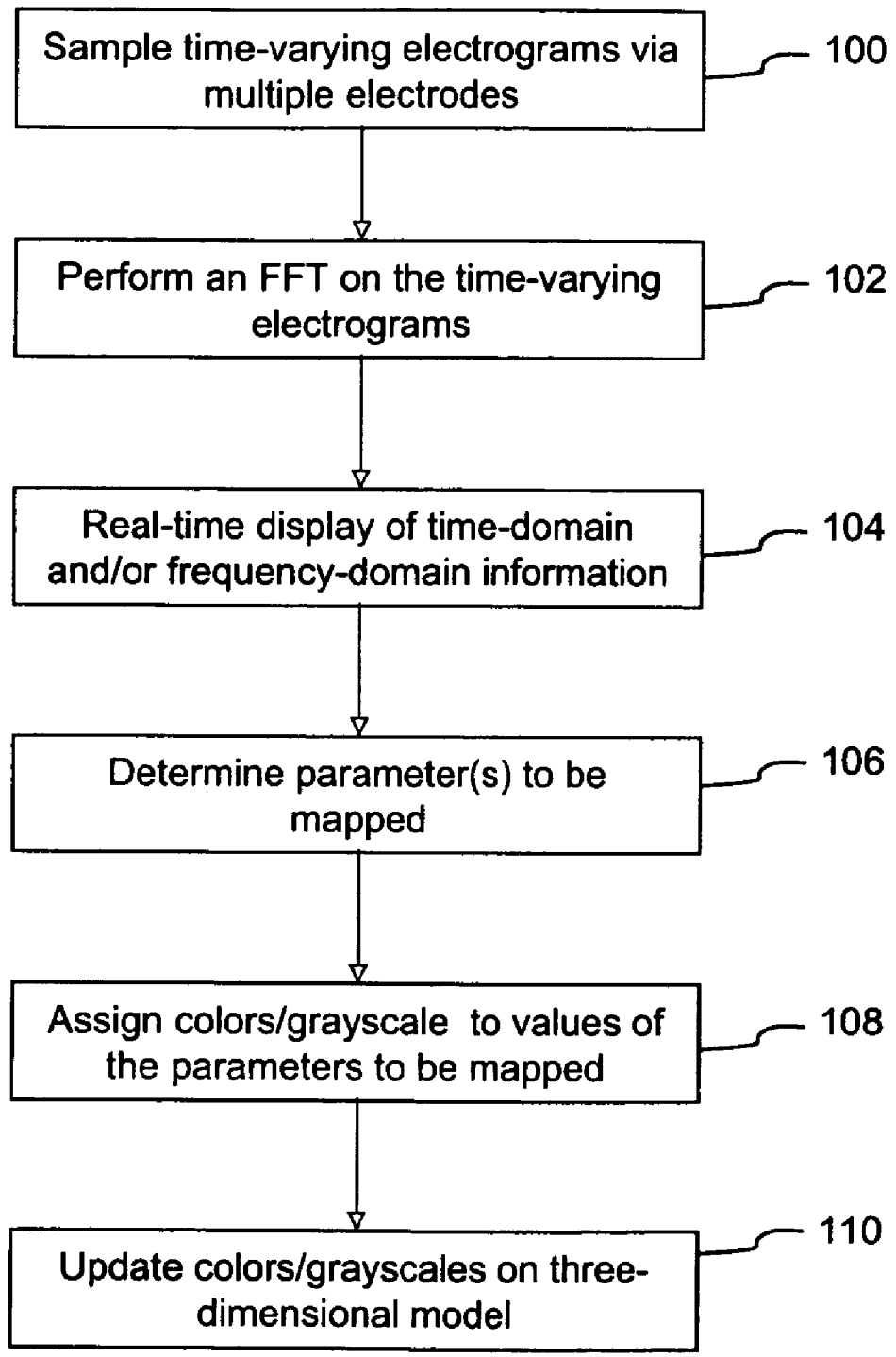
FIG. 10 shows a method for collecting electrograms and mapping time-domain and/or frequency-domain electrogram information on a three-dimensional model.

FIG. 10 shows one example of a method for determining information from a time-varying electrogram in the time-domain and/or frequency-domain and mapping that information onto a three-dimensional model (e.g., a heart). In operation 100, a number of electrodes (e.g., contact or non-contact, unipolar or bipolar mapping electrodes) are used to sample a time-varying electrogram signal. The electrogram signal, for example, may be sampled for multiple sites along the wall of the heart and/or the surrounding vasculature.

An FFT is then performed over a time period of the time-varying electrogram to determine frequency-domain information for that electrogram in operation 102. A real-time display of the time-domain and/or frequency-domain information may be displayed in operation 104. One or more parameters are then determined in operation 106. Exemplary parameters are described above and include, for example, a time difference between a roving electrode and a reference electrode; the peak-to-peak voltage of the roving electrode; the peak negative voltage of the roving electrode; CFE information; a dominant frequency of an electrogram signal; a maximum peak amplitude at the dominant frequency; a ratio of energy in one band of the frequency-domain to the energy in a second band of the frequency-domain; a low-frequency or high-frequency passband of interest; a frequency with the maximum energy in a passband; a number of peaks within a passband; an energy, power, and/or area in each peak; a ratio of energy and/or area in each peak to that in another passband; and a width of each peak in a spectrum. Colors, shades of colors, and/or grayscales are assigned to values of the parameters to be identified in operation 108, and colors, shades of colors, and/or grayscales corresponding to the parameters for the electrograms sampled by the electrodes are updated on a three-dimensional model (e.g., of a heart) continuously and in real time in operation 110.

One particular area of interest is the mapping of areas of the heart comprised of autonomic nerve cells. ECG information may be mapped to identify the foci of electrical propagation through the heart. The initiation points for electrical signals will generally be autonomic cell bundles, or ganglia plexi. To the extent that any arrhythmia is caused by a malfunction in autonomic cells, the ability to detect this malfunction can significantly aid in the efficacy of treatment and minimize the scope of treatment. A particular advantage to mapping the complex fractionated electrograms in the frequency-domain is the ability to quickly identify and locate such areas of arrhythmia. For example, if it is determined that a specific autonomic bundle is the source of fibrillation, targeting this area of initial neural input instead of treating multiple areas of fibrillar tissue can substantially reduce the number of lesions required to treat the condition.

As discussed above, electrophysiology data can be very useful in locating tissue that may require treatment. A challenge, however, exists with mapping the electrophysiology data onto the three dimensional model of the heart. A projection process in accordance with the present invention will now be described.

As described above, the electrodes of at least one EP catheter are moved over the surface of the heart and while in motion they detect the electrical activation of the heart or other EP signals on the surface of the heart. During each measurement, the real-time location of the catheter electrode is noted along with the value of the EP voltage or signal. The collection of location points and the associated measurements are referred to herein as the "EP data set." This data is then projected onto a surface of the three-dimensional model corresponding to the location of the electrode when the sampled EP data was taken. Since this model was not created while the locating surface electrodes are energized, a projection process may be used to place the electrical information on the nearest heart surfaces represented by the geometry. In one exemplary embodiment, for example, each point on the surface of the three-dimensional model is colored or gray-shaded according to the value of the single nearest location in the EP data set. This new point is used as the "location" for the presentation of EP data in the images presented to the physician.

In another embodiment, the EP data is mapped onto the three-dimensional model using a new and improved technique. Because the EP data is measured at points that may not be the same set of physical locations used to generate the three-dimensional model, the EP data must be projected onto a surface of the three-dimensional model. In this preferred embodiment, the EP data is projected onto the three-dimensional model for display purposes. The EP data values (peak voltage, activation time, maximum frequency, or other quantities) must also be interpolated onto the points of the three-dimensional geometry. Once the EP data is projected onto the three-dimensional model, the EP data may be converted into colors and rendered according to standard computer graphics techniques. A way to relate the three-dimensional model to the EP data structure must be determined. For many surface-interpolation problems, it is desirable to generate a good triangulation of the data points—connecting them into triangles which fill the x-y plane (in 2D). Then the data value can be approximated at any point in the plane using a smoothly weighted average of the three endpoints of its triangle. This triangular based interpolation is known as barycentric interpolation, although it is contemplated that other known methods of interpolation could be used. In ordinary 2D space, a particular triangulation called the Delaunay triangulation is commonly used and is known to give optimal results. The Delaunay triangulation is closely related to the Voronoi diagram, the set of regions surrounding each data point that are closer to that data point than any other. In particular, each pair of data points whose Voronoi regions border each other is connected by an edge in the Delaunay triangulation. But it is believed that there are no known algorithms for computing a Delaunay triangulation on arbitrary and complex surfaces such as the three-dimensional models of the heart as described in connection with this invention. The method of this preferred embodiment computes a good approximation to the Delaunay triangulation as follows. Each EP data point is projected to its closest point on the three-dimensional model, and those projected points are searched to determine Voronoi neighbors. A vertex is selected in the three-dimensional model, and the EP data map is searched for the two EP data points that are closest to the vertex in the three-dimensional model. Generally, the EP data points that are neighboring the selected vertex are searched first, and then generally, the neighbors of neighbors are searched, until the two closest EP data points are found. With high likelihood, those data points have Voronoi regions that border each other, and so the two points are connected with a Delaunay edge. The process is repeated for each of the other vertices in the three-dimensional model. Then, a plurality of triangles are formed out of this set of Delaunay edges, knowing that each edge should be part of exactly two triangles. If the resulting triangulation has any "holes"—cycles of four or more edges not containing any triangles—the holes may be filled by recursively adding the shortest new edge connecting two data points of the cycle. This is necessary because the two-closest-data-point algorithm may not discover every Delaunay edge, although nearly all edges it does discover turn out to be Delaunay edges. Once the EP data points have been have been collected into this triangulation, the measured data may be interpolated onto each vertex of the three-dimensional model. Most vertices will be interior to one of the Delaunay triangles, and will be interpolated using EP data measured at each of the triangle's three data points. Some vertices may be sufficiently close to a triangle edge (e.g., it lies on or very close to the triangle edge), such that the value to be assigned will be bi-linearly interpolated from the respective measurements of the two endpoints. Preferably, a threshold may be set to dictate how close the vertex must be to an edge before bilinear interpolation is applied. A few vertices may be closer to a data point than any edge or triangle, in which case, the vertices will be assigned the same EP data as the close data point. Preferably, a threshold may be set to dictate how close the vertex must be to a measurement point before the value of the measurement point will be assigned. Once EP data values have been assigned to a plurality of points in the three-dimensional model, then a robust color map may be generated, and preferably, the color map is smoothed using a smoothing algorithm to provide a clinically reasonable color rendering, one in which the points in the three-dimensional model get their color only from measurements that were taken at nearby measurement points.

Figure 11:
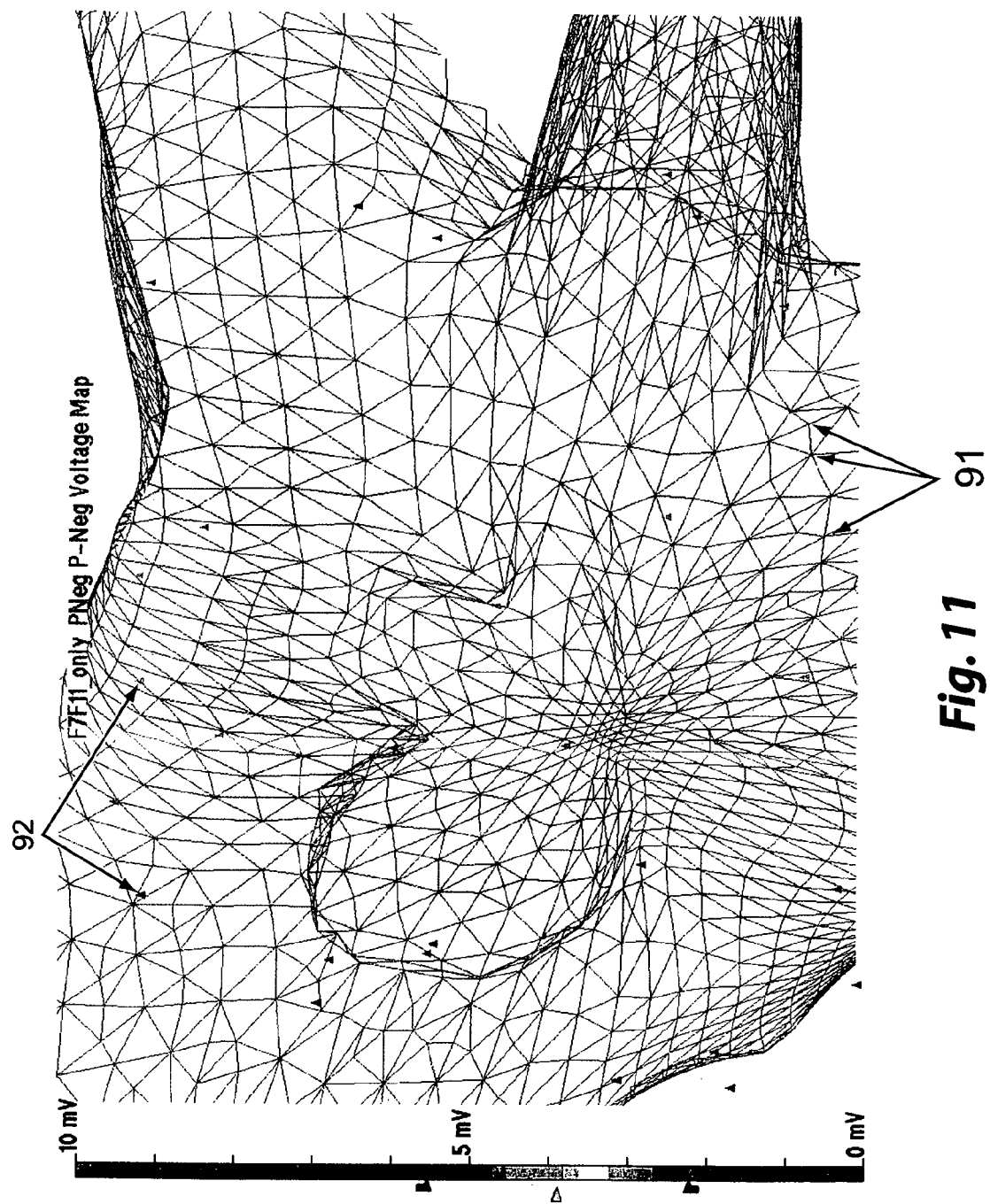
FIG. 11 illustrates a three-dimensional model of a portion of a heart. An identical color version of FIG. 11 (without reference numbers) is also submitted herewith.

The embodiment described in the previous paragraph will now be discussed in the context of FIGS. 11-14. FIG. 11 is a three-dimensional model of a portion of a heart, in which the location points 91 have been connected using triangulation. This surface may be re-sampled over a more uniform grid and further may be interpolated to give a reasonably smooth surface stored as a three dimensional model for presentation to the physician during the same or a later procedure. The re-sampled surface generally has a greater number of data points. The resampled surface may also be processed using a smoothing algorithm, which will give the geometry a smoother appearance. Such a three dimensional model, for example, provides an estimated boundary of the interior of the heart region from the set of points. Markers 92 which represent data measurement points within an EP data set have been superimposed upon the three-dimensional model in FIG. 11. As previously explained, the locations of the data measurement points (represented by markers 92) for the EP data set generally are not at the same locations as location points 91. Thus, markers 92 are sometimes located wholly within a triangle, and other times, appear on or near an edge of a triangle.

Figure 12:
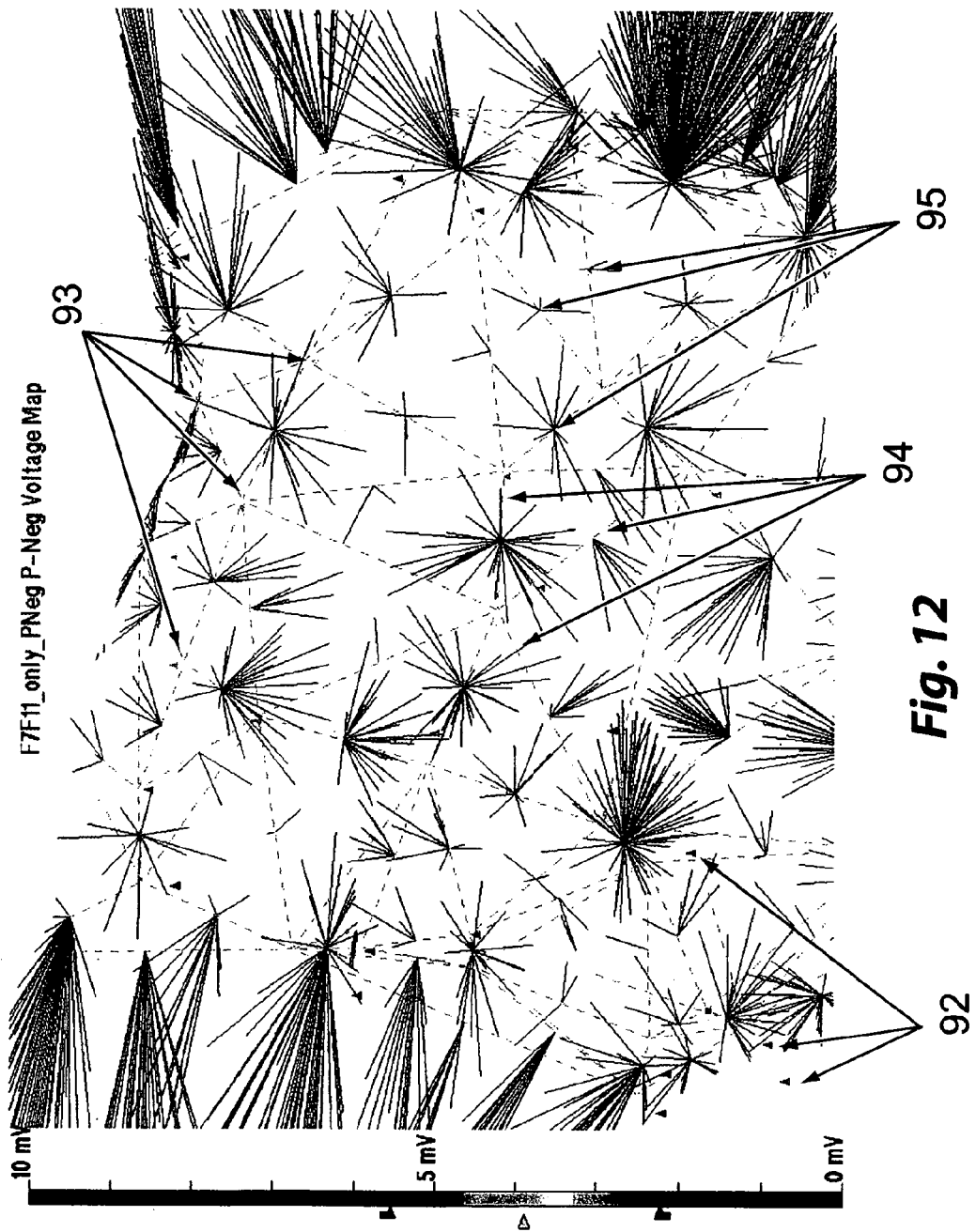
FIG. 12 illustrates an electrophysiology data map for the same portion of the heart shown in FIG. 11. An identical color version of FIG. 12 (without reference numbers) is also submitted herewith.

FIG. 12 shows the EP data set which comprises a series of measurement points 93, each of which has a corresponding voltage level. The voltage level is represented by marker 92, whose color is varied to indicate the voltage level.

Understanding that the EP data set depicted in FIG. 12 is the same overall geometry as that of FIG. 11, it may be visualized that the measurement points 93 of the EP data set, though generated using the same region of the same heart, do not correspond to the location points 91 of the three-dimensional model. It is the lack of a one-to-one positional correspondence that generates a need to project the measured EP data onto the three-dimensional model. To assist in the projection process, a location point 91 is selected from the plurality of location points 91 that comprise the three-dimensional model of FIG. 11. Next, the location of the selected location point 91 is compared to the location of at least a subset of the plurality of measurement points 93 in order to determine which are the two measurement points 93 that are closest to the selected location point 91. The pair of closest measurement points are deemed to form a Delaunay edge 94 (which is depicted by a green line on FIG. 12); it is highly likely that the identified pair of closest measurement points 93 are Voronoi neighbors. The closest measurement points may be identified using any number of algorithms designed to evaluate distances, including, for example, a Kirsanov-Hoppe or Fast Marching geodesic algorithm. The identification of pairs of measurement points based on their proximity to selected location points may be repeated to identify additional Delaunay edges. In the process of assessing closest pairs of measurement points for each location point, a plurality of triangles will likely be formed. If after this algorithm, there remain location points which are not part of a triangle, then triangular relationships may be formed by drawing lines to the other measurement points, giving preference to those measurement points which may be connected using shortest distance lines (with preferences given to the creation of triangle edges that are shorter in length).

Figure 13:
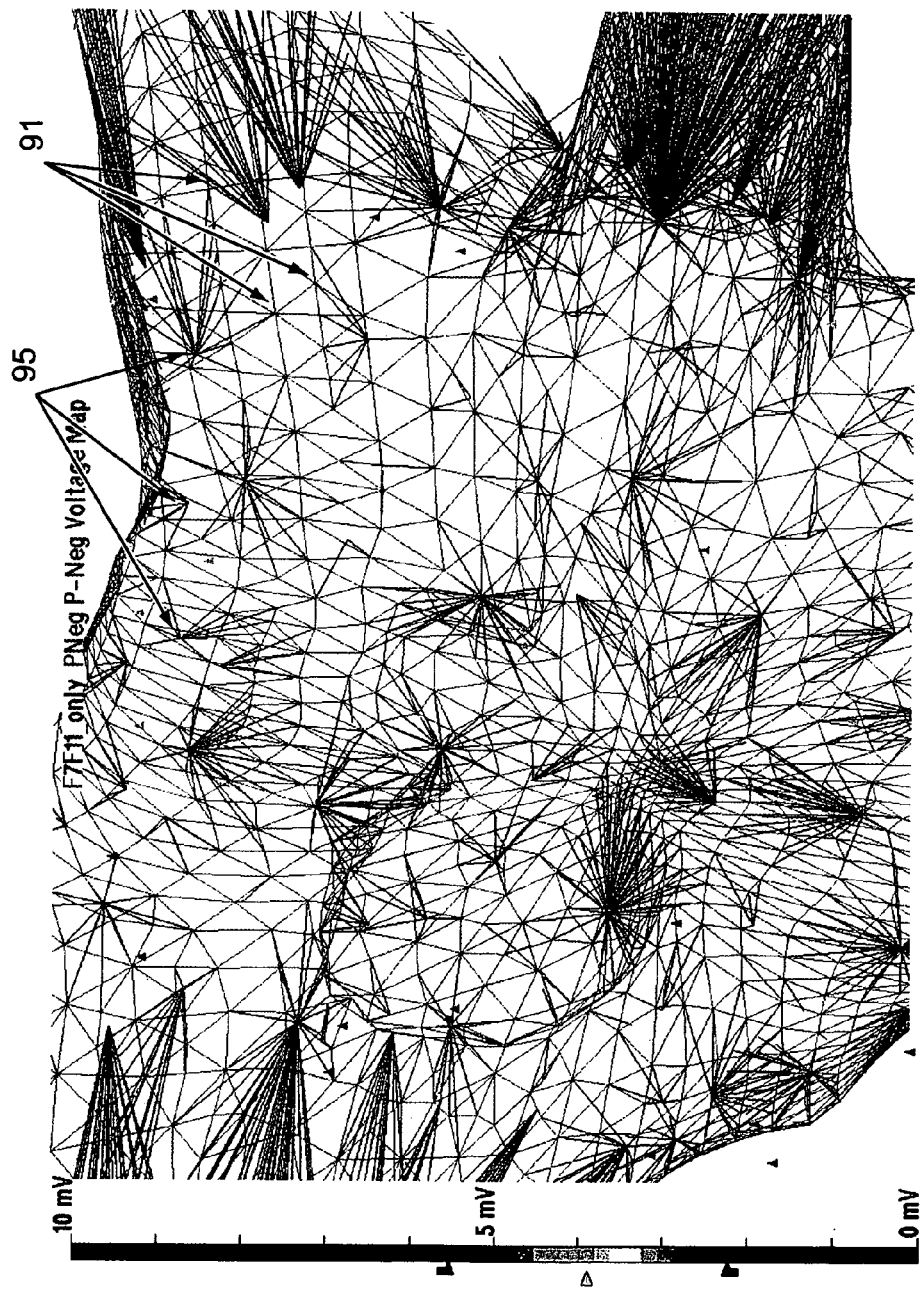
FIG. 13 contains the three-dimensional model of FIG. 11 upon which distance lines have been drawn from midpoints that are measured using FIG. 12. An identical color version of FIG. 13 (without reference numbers) is also submitted herewith.

While the proximity relationships between selected location points 91 and their respective pairs of closest measurement points 93 may be tracked in a variety of ways, the relationship are depicted graphically in both FIG. 12 and FIG. 13. On FIG. 12, the midpoints 95 of most Delaunay edges have at least one, and typically, several lines (they appear in dark, red ink) that contact the midpoint 95. These lines represent connections to various location points in the three-dimensional model. The existence of a line to a particular location point means that for that particular location point, it was determined that the pair of closest measurement points was the pair that forms the identified Delaunay edge. The same red lines are shown in FIGS. 12 and 13, but FIG. 12 shows them with the Delaunay edges and FIG. 13 with the three-dimensional model. FIG. 13 contains the three-dimensional model of FIG. 11 upon which distance lines have been imposed to identify the associations between selected location points in the three-dimensional model and the Delaunay edges that are closest to the selected location points. These associations are used when the measured data of the EP map is projected onto the location points of the three-dimensional model. These red lines only determine which Delaunay edges are used in the triangulation; they are not used to indicate from which Delaunay edges the various location points of the three-dimensional model are interpolated.

Figure 14:
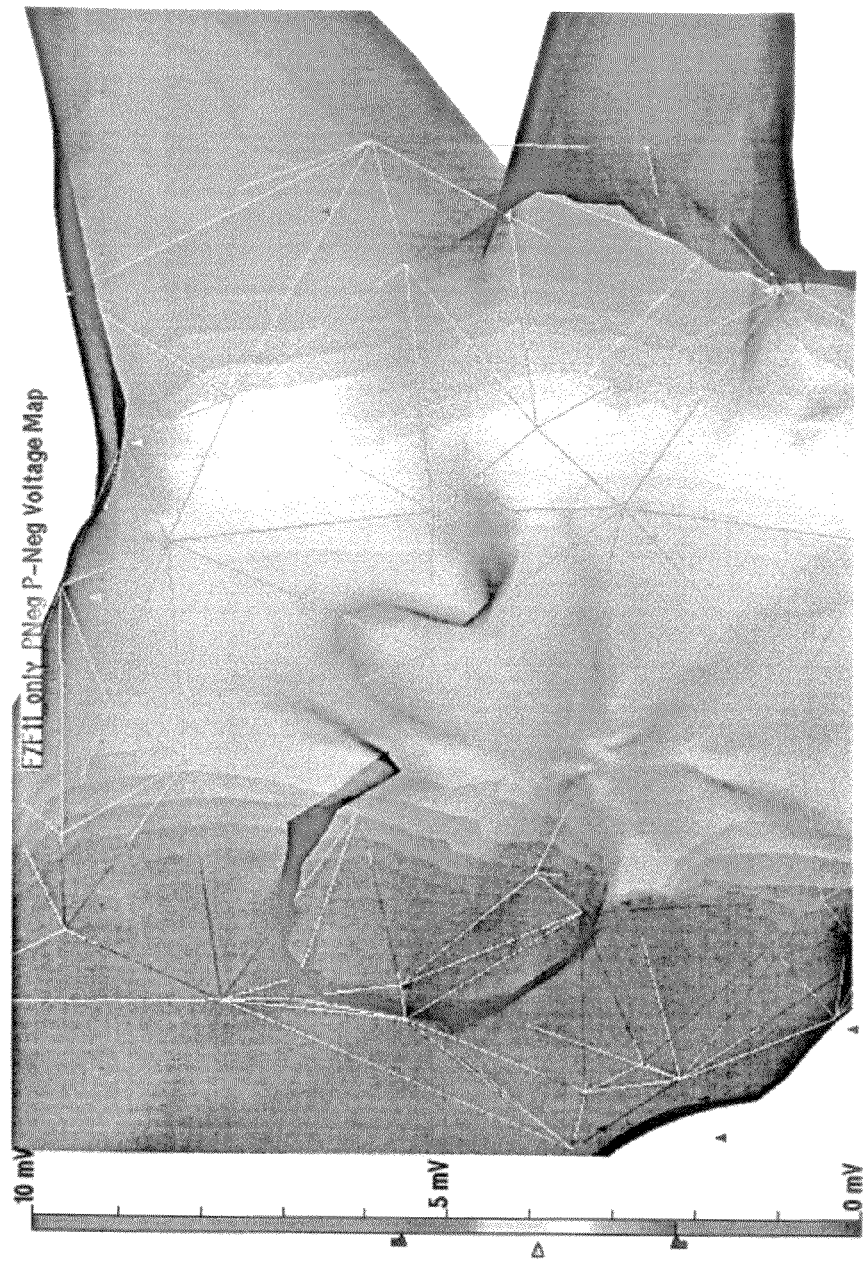
FIG. 14 shows a voltage map for the same portion of the heart as shown in FIG. 11, in which the electrophysiology data map from FIG. 12 has been projected on to the three-dimensional model of FIG. 11. An identical color version of FIG. 14 (without reference numbers) is also submitted herewith.

The actual projection of EP data values will be described next. Each location point in the three-dimensional model is assessed relative to the triangles that have been used to model the EP data set. Conceptually, if the three-dimensional model is superimposed on the triangulated model of the EP data set, the relationship between the location points and the triangles is much easier to visualize. Most location points 91 will be within the interior of one of the triangles of the triangulated model of the EP data set, and the EP data value to be assigned to such location points 91 may be interpolated using barycentric interpolation based on the measured values of the three vertices (the measurement locations 93) of the triangle. Barycentric interpolation is known in the art, and is a preferred method. However, it is contemplated that other known methods of interpolation could be used as well. Some location points 91 may be so close to a triangle edge (e.g., it lies on or very close to the triangle edge), such that the value to be assigned will be bi-linearly interpolated from the respective measured EP data values of the two endpoints of the edge. A few location points 91 may be closer to a measurement point than any edge or triangle, in which case, the location points 91 will be assigned the same EP data value as was measured at the closest measurement point. Once EP data values have been assigned to a plurality of points in the three-dimensional model (and preferably, all of the location points of the three-dimensional model), then the three-dimensional model (and its corresponding assigned EP data values) may be submitted to a coloring program which can color the three-dimensional model based on its assigned EP data levels (e.g., peak voltage, activation time, maximum frequency, or other quantities). FIG. 14 represents the output from a coloring program, wherein the coloring represents different voltage levels that were assigned by projecting the EP data map of FIG. 12 onto the three-dimensional model of FIG. 11.

In yet another embodiment, the EP data is mapped onto the three-dimensional model using a technique involving subdividing the three-dimensional model. Specifically, the three-dimensional model is subdivided using triangulation in such a way as to make all EP data points vertices in a subdivided three-dimensional model. Then, the subdivided three-dimensional model may be processed using a mesh-coarsening or decimation algorithm that allows one to specify the output vertex set—which will be specified as being exactly the set of EP data points. The decimation program may then decide the proper connectivity for the points on the three-dimensional model. It is preferred in this embodiment that each vertex in the EP data be projected onto the closest vertex or edge of the subdivided three-dimensional model using the Kirsanov-Hoppe or Fast Marching geodesic algorithm. The output of the decimation program may then be submitted to a coloring program which can color the three-dimensional model based on its voltage levels. It is also contemplated that Delaunay edges that are longer than a predetermined distance threshold be disallowed.

Although multiple embodiments of this invention have been described above with a certain degree of particularity, those skilled in the art could make numerous alterations to the disclosed embodiments without departing from the spirit or scope of this invention. For example, while the description above describes data being mapped to a three-dimensional model, data may be mapped to any map including, but not limited to, a two- or three-dimensional, static or time-varying image or model. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method for mapping electrophysiological information on a three-dimensional model comprising:

A) obtaining a three-dimensional model of a portion of an anatomy comprising position information for a plurality of location points on a surface of the portion of the anatomy;

B) obtaining an electrophysiology map comprising position information for a plurality of measurement points and electrophysiology measurements made at each of the plurality of measurement points;

C) choosing a location point from the plurality of location points in the three-dimensional model and determining a pair of closest measurement points from the electrophysiology map;

D) defining an edge between the pair of closest measurement points;

E) repeating steps C) and D) for at least a first subset of the plurality of location points in the three-dimensional model, thereby defining a plurality of edges connecting at least some of the plurality of measurement points within the electrophysiology map;

F) defining a plurality of polygons from the plurality of edges;

G) identifying one of the plurality of location points from the three-dimensional model, identifying one of the plurality of polygons whose edges surround the identified location point, and assigning an electrophysiology level to the identified location point using electrophysiology measurements measured at one or more vertices of the identified polygon; and H) repeating step (G) for at least a second subset of the plurality of location points in the three-dimensional model.

2. The method according to claim 1, wherein the step of assigning an electrophysiology level to the identified location point using electrophysiology measurements measured at one or more vertices of the identified polygon comprises assigning an electrophysiology level to the identified location point using barycentric interpolation.

3. The method according to claim 1, wherein the step of assigning an electrophysiology level to the identified location point using electrophysiology measurements measured at one or more vertices of the identified polygon comprises:
identifying a closest edge of the identified polygon to the identified location point; and
assigning an electrophysiology level to the identified location point using linear interpretation.

4. The method according to claim 1, wherein the step of assigning an electrophysiology level to the identified location point using electrophysiology measurements measured at one or more vertices of the identified polygon comprises:
identifying a closest vertex of the identified polygon to the identified location point; and
assigning the identified location point an electrophysiology level equal to an electrophysiology level at the closest vertex.

5. The method according to claim 1, further comprising:
assigning a color or grayscale to each location point within the second subset of the plurality of location points based on a relative magnitude of the electrophysiology level assigned to each location point within the second subset of the plurality of location points; and
presenting the three-dimensional model using the colors or grayscales assigned to each location point within the second subset of the plurality of location points.

6. The method according to claim 1, wherein the step of obtaining an electrophysiology map comprises:
inserting an electrode into a patient;
placing the electrode at a plurality of measurement points;
receiving position information for each of the plurality of measurement points;
receiving electrophysiology measurements at each of the plurality of measurement points; and
associating the electrophysiology measurements with the respective measurement points at which the electrophysiology measurements were measured.

7. The method according to claim 1, wherein the step of obtaining a three-dimensional model of a portion of an anatomy comprises:
inserting an electrode into a patient;
placing the electrode at a plurality of location points within the patient;
receiving position information for each of the plurality of location points; and
generating a three-dimensional model of a portion of an anatomy comprising position information for each of the plurality of location points.

8. The method according to claim 1, wherein the step of defining a plurality of polygons from the plurality of edges comprises defining a plurality of triangles from the plurality of edges.

9. The method according to claim 1, wherein the step of obtaining a three-dimensional model of a portion of an anatomy comprises using an electrical-field based localization system to generate the three-dimensional model of the portion of the anatomy.

10. A system for mapping electrophysiological information on a three-dimensional model, the system comprising:
a modeling processor to generate a three-dimensional model of at least a portion of an anatomy comprising position information for a plurality of location points on a surface of the portion of the anatomy;
an electrophysiology measurement device for generating an electrophysiology map comprising position information for a plurality of measurement points and electrophysiology measurements made at the plurality of measurement points, the electrophysiology measurements being associated with the respective measurement points at which they were measured;
an edge processor to process at least a first subset of the plurality of location points on the surface of the anatomy; to determine, for each location point within the first subset of the plurality of location points, a pair of closest measurement points in the electrophysiology map; and to define an edge connecting the pair of closest measurement points;
a geometry processor to define a plurality of polygons from a plurality of edges defined by the edge processor; and
a projection processor to assign an electrophysiology level to each location point within a second subset of the plurality of location points based upon electrophysiology measurements measured at one or more vertices of a polygon from the plurality of polygons surrounding each location point within the second subset of the plurality of location points.

11. The system according to claim 10, wherein the projection processor assigns an electrophysiology level to each location point within the second subset of the plurality of location points based upon barycentric interpolation.

12. The system according to claim 10, wherein the projection processor assigns an electrophysiology level to each location point within the second subset of the plurality of location points based upon linear interpolation.

13. The system according to claim 10, wherein the geometry processor defines a plurality of triangles from the plurality of edges defined by the edge processor.

* * * * *